United States Patent
Sutton et al.

(10) Patent No.: US 9,330,523 B2
(45) Date of Patent: May 3, 2016

(54) WAGERING GAME MACHINE WITH BIOFEEDBACK-AWARE GAME PRESENTATION

(75) Inventors: James E. Sutton, Cary, IL (US); Samuel Leopold, Chicago, IL (US); Gene Rigsby, Chicago, IL (US)

(73) Assignee: Bally Gaming, Inc., Las Vegas, NV (US)

( * ) Notice: Subject to any disclaimer, the term of this patent is extended or adjusted under 35 U.S.C. 154(b) by 769 days.

(21) Appl. No.: 13/619,250

(22) Filed: Sep. 14, 2012

(65) Prior Publication Data

US 2013/0072292 A1 Mar. 21, 2013

Related U.S. Application Data

(63) Continuation of application No. 11/276,250, filed on Feb. 21, 2006, now Pat. No. 8,298,078.

(60) Provisional application No. 60/657,040, filed on Feb. 28, 2005, provisional application No. 60/732,756, filed on Nov. 2, 2005.

(51) Int. Cl.
| | |
|---|---|
| A63F 9/24 | (2006.01) |
| A63F 13/00 | (2014.01) |
| G06F 17/00 | (2006.01) |
| G06F 19/00 | (2011.01) |
| G09B 19/00 | (2006.01) |
| G07F 17/32 | (2006.01) |
| A61B 5/16 | (2006.01) |
| A61B 5/00 | (2006.01) |

(52) U.S. Cl.
CPC ............... *G07F 17/32* (2013.01); *A61B 5/165* (2013.01); *A61B 5/486* (2013.01); *G07F 17/3206* (2013.01); *G07F 17/3216* (2013.01); *G07F 17/3239* (2013.01)

(58) Field of Classification Search
CPC ............ G07F 17/3239; G07F 17/3206; G07F 17/3216; A61B 5/165; A61B 5/486
USPC .......................................................... 434/238
See application file for complete search history.

(56) References Cited

U.S. PATENT DOCUMENTS

| | | |
|---|---|---|
| 5,001,632 A | 3/1991 | Hall-Tipping |
| 5,318,295 A | 6/1994 | Hofer |
| 5,362,069 A | 11/1994 | Hall-Tipping |
| 6,142,876 A | 11/2000 | Cumbers |
| 6,234,900 B1 | 5/2001 | Cumbers |

(Continued)

OTHER PUBLICATIONS

"U.S. Appl. No. 11/276,250, Examiners Interview Summary mailed Nov. 10, 2011", 3 pgs.

(Continued)

*Primary Examiner* — Omkar Deodhar
*Assistant Examiner* — Wei Lee
(74) *Attorney, Agent, or Firm* — Nixon Peabody LLP

(57) ABSTRACT

A computerized wagering game system includes a gaming module comprising gaming code which is operable when executed on to conduct a wagering game on which monetary value can be wagered, and a biofeedback module operable to track at least one biometric characteristic of a game player. The wagering game is further operable to alter presentation of the wagering game based on changes in the at least one biometric characteristic. A mood enhancement module is operable to provide energy to a wagering game player at a frequency designed to provide a mood enhancing effect.

20 Claims, 5 Drawing Sheets

(56) References Cited

U.S. PATENT DOCUMENTS

| | | |
|---|---|---|
| 6,350,199 B1 | 2/2002 | Williams |
| 6,554,705 B1 | 4/2003 | Cumbers |
| 6,702,767 B1 | 3/2004 | Douglas et al. |
| 6,752,716 B1 | 6/2004 | Nishimura et al. |
| 6,843,726 B1 | 1/2005 | Nomi et al. |
| 7,189,189 B1 | 3/2007 | Mathers |
| 7,502,643 B2 | 3/2009 | Farringdon et al. |
| 7,828,645 B2 | 11/2010 | Walker et al. |
| 2002/0160883 A1 | 10/2002 | Dugan |
| 2002/0196342 A1 | 12/2002 | Walker et al. |
| 2003/0064805 A1 | 4/2003 | Wells |
| 2003/0073489 A1 | 4/2003 | Hecht et al. |
| 2003/0131265 A1 | 7/2003 | Bhakta |
| 2003/0186784 A1 | 10/2003 | Ogawa |
| 2003/0195040 A1 | 10/2003 | Breving |
| 2003/0199295 A1* | 10/2003 | Vancura ............ 463/16 |
| 2003/0228901 A1 | 12/2003 | Walker et al. |
| 2004/0077934 A1* | 4/2004 | Massad ............ 600/300 |
| 2004/0166936 A1* | 8/2004 | Rothschild et al. ....... 463/35 |
| 2004/0209692 A1 | 10/2004 | Schober et al. |
| 2004/0254014 A1 | 12/2004 | Quraishi et al. |
| 2006/0063644 A1 | 3/2006 | Yang |
| 2006/0281543 A1 | 12/2006 | Sutton et al. |

OTHER PUBLICATIONS

"U.S. Appl. No. 11/276,250, Final Office Action mailed Jan. 5, 2011", 17 pgs.

"U.S. Appl. No. 11/276,250, Final Office Action mailed Oct. 30, 2009", 15 pgs.

"U.S. Appl. No. 11/276,250, Final Office Action mailed Nov. 28, 2008", 13 pgs.

"U.S. Appl. No. 11/276,250, Non Final Office Action mailed Aug. 2, 2011", 19 pgs.

"U.S. Appl. No. 11/276,250, Non-Final Office Action mailed Mar. 12, 2009", 14 pgs.

"U.S. Appl. No. 11/276,250, Non-Final Office Action mailed May 8, 2008", 11 pgs.

"U.S. Appl. No. 11/276,250, Non-Final Office Action mailed May 26, 2010", 17 pgs.

"U.S. Appl. No. 11/276,250, Notice of Allowance mailed Jun. 25, 2012", 11 pgs.

"U.S. Appl. No. 11/276,250, Response filed Feb. 3, 2009 to Final Office Action mailed Nov. 28, 2008", 12 pgs.

"U.S. Appl. No. 11/276,250, Response filed Apr. 30, 2010 to Final Office Action mailed Oct. 30, 2009", 15 pgs.

"U.S. Appl. No. 11/276,250, Response filed Jun. 6, 2011 to Final Office Action mailed Jan. 5, 2011", 15 pgs.

"U.S. Appl. No. 11/276,250, Response filed Jun. 12, 2009 to Non Final Office Action mailed Mar. 12, 2009", 13 pgs.

"U.S. Appl. No. 11/276,250, Response filed Aug. 8, 2008 to Non Final Office Action mailed May 8, 2008", 16 pgs.

"U.S. Appl. No. 11/276,250, Response filed Oct. 26, 2010 to Non Final Office Action mailed May 26, 2010", 15 pgs.

"U.S. Appl. No. 11/276,250, Response filed Nov. 2, 2011 to Non Final Office Action mailed Aug. 2, 2011", 20 pgs.

* cited by examiner

WAGERING GAME MACHINE WITH BIOFEEDBACK-AWARE GAME PRESENTATION

RELATED APPLICATIONS

This application is a continuation of U.S. patent application Ser. No. 11/276,250, filed on Feb. 21, 2006 now U.S. Pat. No. 8,298,078, which claims priority under 35 U.S.C. 119(e) from U.S. Provisional Application Ser. No. 60/657,040 filed Feb. 28, 2005, and from U.S. Provisional Application Ser. No. 60/732,756 filed Nov. 2, 2005, which applications are incorporated herein by reference in their entireties.

FIELD OF THE INVENTION

The invention relates generally to computerized wagering game machines, and more specifically to a wagering game machine utilizing biofeedback in varying game play.

LIMITED COPYRIGHT WAIVER

A portion of the disclosure of this patent document contains material to which the claim of copyright protection is made. The copyright owner has no objection to the facsimile reproduction by any person of the patent document or the patent disclosure, as it appears in the U.S. Patent and Trademark Office file or records, but reserves all other rights whatsoever. Copyright 2006, WMS Gaming, Inc.

BACKGROUND

Computerized wagering games have largely replaced traditional mechanical wagering game machines such as slot machines, and are rapidly being adopted to implement computerized versions of games that are traditionally played live such as poker and blackjack. These computerized games provide many benefits to the game owner and to the gambler, including greater reliability than can be achieved with a mechanical game or human dealer, more variety, sound, and animation in presentation of a game, and a lower overall cost of production and management.

The elements of computerized wagering game systems are in many ways the same as the elements in the mechanical and table game counterparts in that they must be fair, they must provide sufficient feedback to the game player to make the game fun to play, and they must meet a variety of gaming regulations to ensure that both the machine owner and gamer are honest and fairly treated in implementing the game. Further, they must provide a gaming experience that is at least as attractive as the older mechanical gaming machine experience to the gamer, to ensure success in a competitive gaming market.

Computerized wagering games often do not rely on the dealer to facilitate game play and to provide an entertaining game playing environment, but rely upon the presentation of the game and environment generated by the wagering game machine itself. Incorporation of audio and video features into wagering games to present the wagering game, to provide help, and to enhance the environment presented are therefore important elements in the attractiveness and commercial success of a computerized wagering game system. Music and environmental effects are also played through speakers in some wagering game systems to enhance or complement a theme of the wagering game. These sounds typically accompany video presentation of the wagering game on a screen, which itself often includes animation, video, and three-dimensional graphics as part of presentation of the wagering game.

The presentation of a wagering game is therefore often a significant factor in attracting a wagering game player to one machine rather than another, and is a key element of the desirability and profitability of a particular wagering game design. High quality game design and engaging themes are priorities in new game development, and presentation of the wagering game is often tailored to ensure that a wagering game player is entertained throughout the gaming experience.

But, many activities can become fatiguing or seem less interesting as time passes. Even wagering games designed to be engaging can seem less interesting over time, and is difficult to anticipate when a wagering game player will begin to feel bored or fatigued and benefit from a change in game presentation. Simple maintenance of a high level of excitement can hasten fatigue, so better methods of managing game presentation to provide a more enjoyable and engaging wagering game experience are therefore desired.

SUMMARY

One example embodiment of the invention comprises a computerized wagering game system including a gaming module comprising gaming code which is operable when executed on to conduct a wagering game on which monetary value can be wagered, and a biofeedback module operable to track at least one biometric characteristic of a game player. The wagering game is further operable to alter presentation of the wagering game based on changes in the at least one biometric characteristic. In another embodiment, a mood enhancement module is operable to provide energy to a wagering game player at a frequency designed to provide a mood enhancing effect.

DETAILED DESCRIPTION

In the following detailed description of example embodiments of the invention, reference is made to specific examples by way of drawings and illustrations. These examples are described in sufficient detail to enable those skilled in the art to practice the invention, and serve to illustrate how the invention may be applied to various purposes or embodiments. Other embodiments of the invention exist and are within the scope of the invention, and logical, mechanical, electrical, and other changes may be made without departing from the subject or scope of the present invention. Features or limitations of various embodiments of the invention described herein, however essential to the example embodiments in which they are incorporated, do not limit the invention as a whole, and any reference to the invention, its elements, operation, and application do not limit the invention as a whole but serve only to define these example embodiments. The following detailed description does not, therefore, limit the scope of the invention, which is defined only by the appended claims.

Various embodiments of the invention seek to provide wagering game players with a more entertaining and personalized gaming experience by use of biofeedback measurements used to control an aspect of the wagering game presentation. In one example, a computerized wagering game system includes a gaming module comprising gaming code which is operable when executed on to conduct a wagering game on which monetary value can be wagered, and a biofeedback module operable to track at least one biometric characteristic of a game player. The wagering game is further operable to alter presentation of the wagering game based on changes in the at least one biometric characteristic.

In another example embodiment, the biofeedback module comprises a mood enhancement module that is operable to provide energy to a wagering game player at a frequency designed to provide a mood enhancing effect. The energy is provided in various embodiments through various transducers or other devices, examples of such including an acoustic transducer, an electromagnetic antenna, a video display, and an air ionizer.

Figure 1:
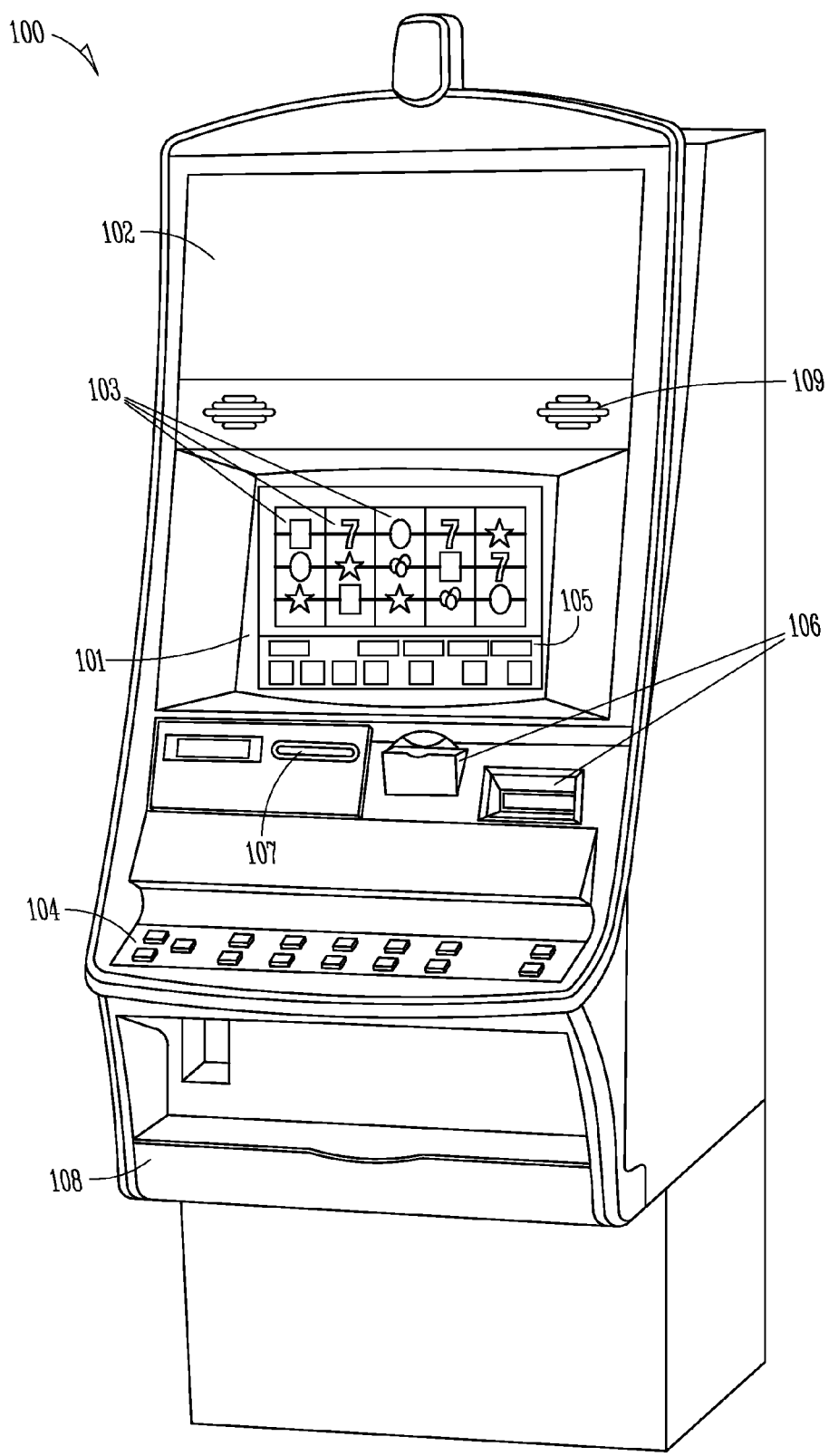
FIG. 1 shows a computerized wagering game machine, as may be used to practice some example embodiments of the invention.

FIG. 1 illustrates a computerized wagering game machine, as may be used to practice some embodiments of the present invention. The computerized gaming system shown generally at 100 is a video wagering game system, which displays information for at least one wagering game upon which monetary value can be wagered on video display 101. Video display 101 is in various embodiments a CRT display, a plasma display, an LCD display, a surface conducting electron emitter display, or any other type of display suitable for displaying electronically provided display information. Further embodiments include a top box display 102, operable to display a second game, bonus game, or other video or graphics. Alternate embodiments of the invention will have other game indicators, such as mechanical reels instead of the video graphics reels shown at 103 that comprise a part of a video slot machine wagering game.

A wagering game is implemented using software within the wagering game system, such as through instructions stored on a machine-readable medium such as a hard disk drive or nonvolatile memory. In some further example embodiments, some or all of the software stored in the wagering game machine is encrypted or is verified using a hash algorithm or encryption algorithm to ensure its authenticity and to verify that it has not been altered. For example, in one embodiment the wagering game software is loaded from nonvolatile memory in a compact flash card, and a hash value is calculated or a digital signature is derived to confirm that the data stored on the compact flash card has not been altered. The wagering game implemented via the loaded software takes various forms in different wagering game machines, including such well-known wagering games as reel slots, video poker, blackjack, craps, roulette, or hold'em games. The wagering game is played and controlled with inputs such as various buttons 104 or via a touchscreen overlay to video screen 101. In some alternate examples, other devices such as a pull arm are used to initiate reel spin in this reel slot machine example, and are employed to provide other input interfaces to the game player.

Monetary value is typically wagered on the outcome of the games, such as with tokens, coins, bills, or cards that hold monetary value. The wagered value is conveyed to the machine through a changer 106 or a secure user identification module interface 107, and winnings are returned via the returned value card or through the coin tray 108. Sound is also provided through speakers 109, typically including audio indicators of game play, such as reel spins, credit bang-ups, and environmental or other sound effects or music to provide entertainment consistent with a theme of the computerized wagering game. In some further embodiments, the wagering game machine is coupled to a network, and is operable to use its network connection to receive wagering game data, track players and monetary value associated with a player, and to perform other such functions.

The video display 101 and the speakers 109 are used to present the wagering game to the game player, and in some embodiments are replaced or supplemented with other features such as mechanical reels in a mechanical reel slot machine to convey game information and entertain the game player. Many wagering game machines also have themes, such as a game centered around a fishing theme or an old west theme. Various video, graphics, sounds, and animations are often presented consistent with the wagering game theme, and various objects such as static art on the machine or reel symbols are often related to the selected theme. The pace of presentation of the game, the animations, the sound effects, and other elements of wagering game presentation are typically under the control of the wagering game system's software, and can be varied according to the software's instruction.

In some embodiments of the invention, various components of a wagering game presentation are varied dependent on biofeedback data collected from the wagering game player. This enables the wagering game to adapt to the excitement level, mood, or present disposition of the wagering game player, and to make the game presentation more enjoyable for the game player.

Figure 2:
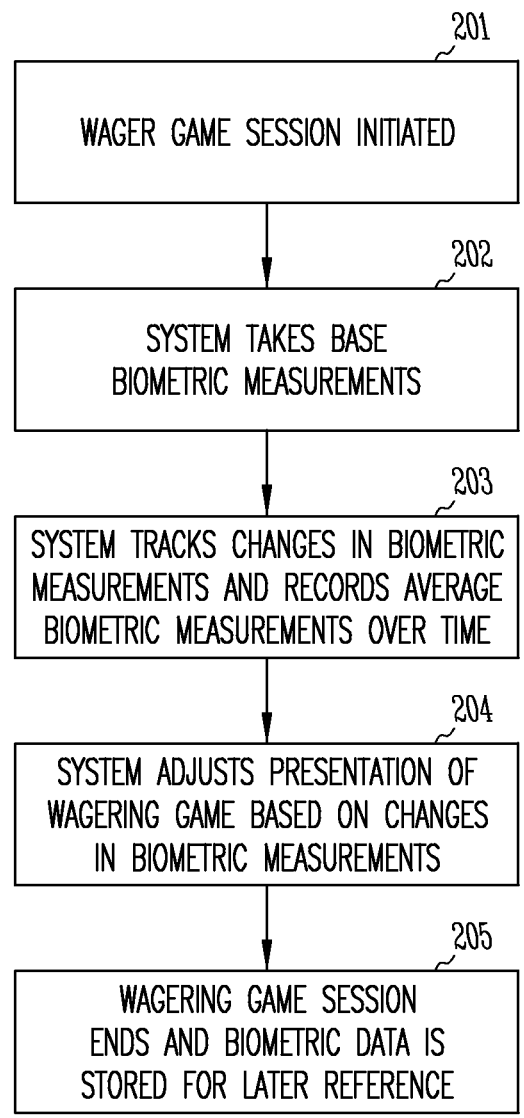
FIG. 2 is a flowchart of a method of operating a computerized wagering game machine including altering presentation of the game via biometric tracking, consistent with some example embodiments of the invention.

FIG. 2 is a flowchart, illustrating an example method of operating a wagering game including changing presentation of the wagering game based on biometric feedback, consistent with an example embodiment of the invention. A wagering game session of play is initiated at 201, which in various embodiments includes depositing monetary value in the wagering game machine such as by depositing tokens, a stored value card, a player identification card, or another such item. The game player then begins game play, and baseline biometric measurements are taken at 202.

The baseline biometric measurements are used as a temporary estimation of "normal" or reference biometric indicators for the wagering game player in this example. In other embodiments, baseline biometric parameters will be stored, such as in a player identification card or in a server such that they can be referenced based on identification of a player at a networked wagering game machine. This enables a baseline to be established over time, and will likely provide more useful baseline biometric data than simply taking a new baseline measurement at the start of each gaming session. The baseline in some such embodiments is a time-averaged biometric measurement, which in some further embodiments includes range information such as a time-averaged standard deviation indicating the normal degree of variability of a particular biometric measurement.

The system of this example therefore tracks biometric measurement changes over time at 203, and uses the time-based average biometric measurement as a baseline. Changes in biometric measurements are therefore not only observable as changes from a previous biometric measurement, but are comparable against a time-weighted average or other baseline biometric measurement throughout a session of game play, and in some further embodiments are comparable in relative magnitude to typical variation from a baseline parameter through use of a standard deviation metric or other such metric. The change from the biometric average is then used to adjust some parameter of game play at 204, such as to change the pace of play, the pace or pitch of music, or the animations presented to the wagering game player.

Figure 3:
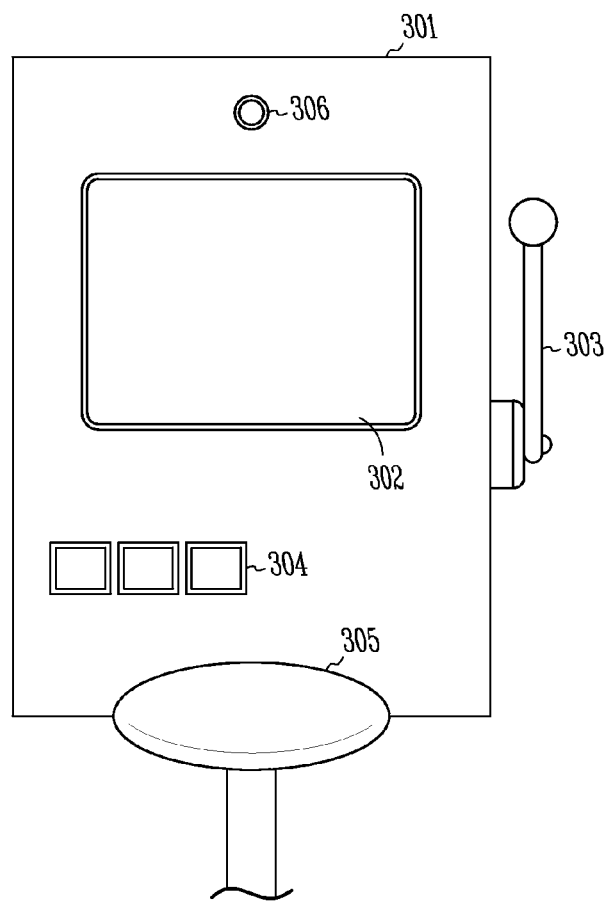
FIG. 3 is a diagram of a wagering game system showing various biometric measurement devices, consistent with some example embodiments of the invention.

FIG. 3 shows a more detailed example of a wagering game system operable to track biometric measurements from a wagering game player, consistent with some embodiments of the invention. The wagering game machine 301 has a touchscreen 302, and various inputs such as a pullarm 303 and buttons 304. The system shown further includes a seat 305, and one or more additional sensors 306, such as a pupil scanner or infrared camera. Biometric sensors, including body temperature monitors, blood pressure monitors, a pulse sensor, or a body movement sensor are incorporated into the player interface devices. For example, a pulse sensor and blood pressure monitor are incorporated here into pullarm 303, such that when the wagering game player pulls the pullarm, biometric measurements are taken and used to adjust presentation of the wagering game. Further, buttons 304 here incorporate various features such as infrared temperature sensors, pulse sensors, or blood pressure sensors for reading a game player's biometric information. The seat 305 includes one or more pressure sensors, which in operation are used to monitor shifting around in the seat during game play.

Additional sensors such as the pupil scanner or infrared camera can be mounted as shown at 306, and used to monitor the pupil diameter of the game player's eye or monitor the infrared profile of the game player's face. It is anticipated that changes in the game player's interest will be reflected in the biometric measurements taken, such as a higher pulse when the game player is excited or a lower pulse when the game player becomes bored. Similarly, body temperature and blood pressure are expected to be higher when a game player is excited, and lower when the game player is calm. Pupil diameter is known to increase when a person is content or happy, and contracts when the person is upset or nervous. Infrared imaging of a game player's face can reveal information regarding the body temperature and blood flow in the game player, where higher perceived body temperature or blood flow indicate dilated blood vessels and higher levels of excitement in the game player.

Certain other factors can influence some biometric measurements, such as a player who has the flu or is drunk. Such players may have elevated body temperatures and dilated blood vessels, but have relatively low pulses and blood pressure. Some embodiments of the invention will therefore consider various combinations of biometric parameters, and in still further embodiments can be used to detect unusual or unsafe conditions such as illness or intoxication in game players. Because monitoring or tracking such parameters related to potential medical or physical condition may be considered confidential or an intrusion into the privacy of the game player by some wagering game players, such information may be limited in the way it is used, such as by being provided only to security personnel for purposes of monitoring the game player while in the gaming facility to ensure the game player's health and safety or for notifying the wait staff that a player may be intoxicated and should not be served any further alcohol.

In a further embodiment, biometric measurements that can indicate identity, such as infrared face scans or pupil/retina scans, can be used to identify a particular game player. This enables the wagering game system to perform a variety of functions based on establishing the identity of a player, from eliminating the need for tracking cards to enhancing security. For example, a player having a certain number of credits or dollars in his account can simply sit at a wagering game machine and have his identity confirmed through the biometric measurements, eliminating the need to carry or protect a player tracking or player value card. In a further embodiment, additional information such as a pin number will be required as a second form of protection for the player's account, ensuring the security and accuracy of the biometric identification.

Identifying a game player using biometric identifiers can also be used to identify known cheats, such as those who have previously had their biometric baseline data measured and stored while playing, or who have simply been photographed or are otherwise recognizable to the wagering game machine, but who have since been banned or restricted from playing wagering games in a particular gaming establishment. This functionality greatly enhances the gaming facility's ability to monitor the premises for known cheats, due to both the relatively low cost of incorporating such functionality into machines and the relatively high cost of paying additional security people who may be more easily fooled or distracted to monitor the gaming establishment. Incorporation of this feature into a large percentage of wagering game systems in a gaming establishment therefore makes it significantly less likely that a known cheat will be able to play a wagering game machine undetected in a gaming establishment equipped with biometric sensing and tracking systems such as those described here.

Figure 4:
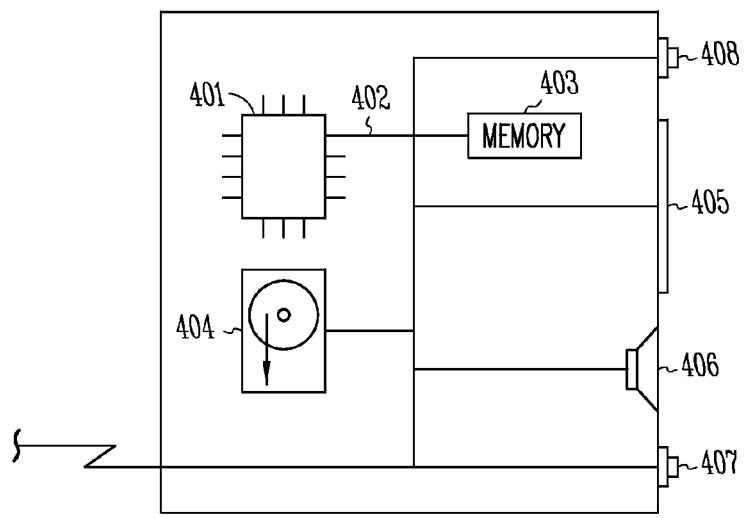
FIG. 4 is a block diagram of a computerized wagering game system employing biometric feedback or mood enhancement functionality, consistent with some example embodiments of the invention.

FIG. 4 shows a block diagram of a wagering game system having a variety of interfaces to a wagering game player, as may be used to practice some embodiments of the invention. A processor 401 is coupled to a computer bus 402, linking the processor to other components such as memory 403 and nonvolatile storage 404. The nonvolatile storage is shown here as a hard disk drive, but in other embodiments is nonvolatile or flash memory, or another suitable nonvolatile storage device. A touchscreen video display 405 and a speaker 406 are coupled for presentation of video and sound to the wagering game player, and button 407 serves as an additional means of player input into the wagering game machine. Additional sensors such as a camera are also incorporated in various embodiments, as shown at 408.

In operation, the processor 401 executes software instructions loaded into memory 403 from nonvolatile storage 404, and controls the other peripheral devices such as the touchscreen display 405 and the speaker 406 at the direction of the software instructions. The software is further operable to receive notice and react to user inputs, such as actuation of the touchscreen 405 or the buttons 407. The wagering game in various embodiments is also operable to receive biometric information from wagering game players, as detected by sensors such as a pulse sensor, a blood pressure sensor, a body temperature sensor, an infrared camera 408, a pupil scanner 408, or a body movement sensor. Many of these sensors can be built into user interface components such as the button 407 or incorporated as a separate information gathering device as shown at 408, and can be used to measure and track various biometric characteristics of a wagering game player during sessions of game play.

The various biometric sensors in this example embodiment are also coupled to the bus 402, enabling the processor and wagering game code to respond to detected biometric data based on the content of the biometric data and the program instructions. The software is thereby able to make various changes in presentation of the wagering game, such as increasing or decreasing the pace or pitch of music, animation, or another aspect of the game presentation, or cutting off play for an obviously intoxicated player.

Consider as an example a theme-based wagering game using a fishing theme with a presentation that varies according to biometric feedback. Reel symbols include fish, bobbers, boats, fishing rods, and other fishing-related items, and are displayed as graphic elements on reels rendered via a touchscreen display. Background animation includes a fisher in a boat on a lake, along with frogs, rippling waves, jumping fish, and other animated objects. Background sounds accompany the frogs, jumping fish, waves, motorized movement of the boat, casting a fishing rod, and other such sounds. Various events or animations such as the boat moving positions on the lake, or the fisher casting the line out again are presented between reel spins, along with other animations including accumulation of fish in qualification for a bonus event.

Any of these events can be varied in pace or in frequency, and the sounds accompanying them can be changed in pitch, volume, in complexity, or in other characteristics to either make presentation of the wagering game more exciting or less exciting. These changes to the presentation of a wagering game are therefore based on biometric measurement readings in various embodiments of the invention so that the wagering game system is able to maintain player interest and excitement in playing the presented game. In this example, the fishing environment may include more elements such as frogs, jumping fish, and seagull noises when the player's biometric characteristics suggest boredom or fatigue, and the same elements may be scaled back when the player is already excited.

Variation of the frequency or energy presented to a wagering game player is used in a further example to enhance the wagering game player's mood or other physical response, through a mood enhancing module. The mood enhancing module is in various embodiments designed to enhance the mood, physical well-being, psychological state, or other such mood-related state of the wagering game player.

In one such embodiment, the wagering game system records the player's voice, and analyzes its spectral content. The mood enhancement module plays missing frequencies through a speaker 406, using a bioacoustic feedback system which is employed to provide frequencies designed to supplement those of the wagering game player's voice. The use of voice-supplementing frequencies is believed in some applications to heighten awareness, to promote a feeling of relaxation, and to cause other feelings of well-being In some further embodiments, records of a particular wagering game player's voice are recorded or the spectral content is stored, so that the spectral content and relationship between spectral components in a wagering game player's voice can be stored and re-used. The data in embodiments where a network is available is stored in some embodiments in a network server, so that a user identification card or other identifier can be used on a variety of wagering game machines within a single establishment or across networked establishments and still benefit from the stored voice data.

In another embodiment, audible or visible beats or oscillations are presented to the wagering game player, such as through the speaker 406 or the touchscreen video display 405. The frequencies are produced as beats when they are formed as the difference between two or more fundamental tones, although frequencies can be produced by sums, products, differences, or other mathematical functions of root tones in further embodiments. In one example, a speaker such as speaker 406 that is unable to produce frequencies below 20 Hz as a pure tone due to its limited frequency response is able to produce higher frequencies that are a certain frequency apart such that the beats produced by their difference are under 20 Hz. A 400 Hz tone and a 401 Hz tone, for example, can be easily produced at loud volume by most full-range speakers, but the resulting 1 Hz difference tone cannot.

It is believed that many frequencies can have significant physiological effects when presented to a person, such as a wagering game player. A variety of frequencies are listed in the table below, along with the areas in which they are believed to have a physiological or mood-altering effect. These example frequencies include brainwave frequencies that are associated with various mental states, and which can be employed under the theory that brainwave entrainment can coax brainwaves to a certain frequency and achieve as a result the mental state associated with that frequency. Healing frequencies are employed to address illnesses or to stimulate regions or systems within the body. Natural phenomena frequencies are frequencies that occur in nature, such as various periods or resonances of biological, geological, and planetary cycles. The example frequencies listed below are but examples of these frequencies, as explained in the cited source listed in the bibliography that follows.

0.1-1 Organ/muscle resonances [SS]
0.1-3 Delta range, according to [NEU+CRI]—deep sleep, lucid dreaming, increased immune functions, hypnosis [NEU]; Decreased awareness of the physical world. Access to unconscious information. Dominant brainwave in infants under one year old. This range normally decreases when we focus, but this doesn't happen when a person with ADD—delta waves actually increase when they try and focus. [CRI]; "Monroe focus 21" [MB2 via DW];
0.16-10—Neuralgias [AT]
0.18-10—Mod. therapy [AT]
0.20-0.26—Dental pain [AT]
0.20-10—Post-traumatics [AT]
0.28-2.15—Alcohol addiction [AT]
0.28-10—Arthritis [AT]
0.30-0.15—Depression [AT]
0.30-10—Cervobrachial syndrome [AT]
0.37-2.15—Drug addiction [AT]
0.40-10—Confusion [AT]
0.45-10—Muscle pain [AT]
Below 0.5—Epsilon range, extraordinary states of consciousness, high states of meditation, ecstatic states of consciousness, high-level inspiration states, spiritual insight, out-of-body experiences, Yogic states of suspended animation. [CNR]
0.5—very relaxing, against headache [MB], for lower back pain [AS]; Thyroid, reproductive, excretory stimulant, whole brain toner [SS]
0.5-1.5 Pain relief [SS+CMP]; endorphins, better hypnosis [SS]
0.5-3 Delta range, according to [RA]
0.5-4 Delta range, according to [SS,PWM+AWI]. Deep dreamless sleep, trance, suspended animation [SS]; Anti-aging. Reduces amount of cortisol, a hormone associated with stress & aging. Increases the levels of DHEA (anti-aging) & melatonin (decreases aging process.) [BAR]; Associated with unconscious mind & sleep state—in conjunction with other frequencies in a waking state, "Delta acts as a form of radar— seeking out information—reaching out to understand on the deepest unconscious level things that we can't understand through thought process." Provides intuition, empathetic attunement & instinctual insight. [AWI]; Conducive to miracle type healing, divine knowledge, inner being & personal growth, rebirth, trauma recovery, "one with the universe" experiences (samadhi), near death experience, characterized by "unknowing", merely a blissful "being" state such as deep sleep or coma. [PWM via DW]

The anti-aging info comes from a Brainwave Generator preset authored by

TheMind2—he uses binaurals at 0.5, 1.0, 1.5, 2.0, 2.5, 3.0, 3.5 & 4.0 HZ. They all play simultaneously.

0.9 Euphoria [SS]

0.95-10—Whiplash [AT]

1-3—Delia: deep, dreamless sleep, trance state, non-REM sleep [??]; profound relaxation, restorative sleep, feelings of tranquility&peace, if one can remain aware [VUG via DW]

There's disagreement over where the delta range begins & ends—[SS,PWM+AWI] list it as 0.5 to 4.0 HZ, [NEU] 0.1 to 3.0 HZ, & [RA] considers it 0.5 to 3.0 HZ.

1.0—Feeling of well-being, pituitary stimulation to release growth hormone; overall view of inter-relationships; harmony & balance [MB]

1.05 Helps hair grow+get its color back [RA]; pituitary stimulation to release growth hormone (helps develop muscle, recover from injuries, rejuvenation effects) [HSW]

1.2—(used on) headaches [RS]

1.45—Tri-thalamic entrainment format. According to Ronald deStrulle, creates entrainment between hypothalamus, pituitary & pineal. May benefit dyslexics+people with Alzheimer's. [MP2]

1.5 Abrahams Universal Healing Rate [SS]; Sleep [NEU]; Those individuals whose ailments have manifested into the fourth stage of Chronic Fatigue, where some form of disease is apparent, experienced a release from the negative sensation of their symptoms when moved into 1.5 HZ. [NYT via NEU]

1.8 Sinus Congestion seems to clear centering around 1.8 HZ [MPT] (tested with binaural beats, primarily)

2.0 Nerve regeneration [NOR]

2.06 Associated with coccyx (small triangular bone at end of the spinal column) [TOS]

2.15-10—Tendovaginatis [AT]

2.30 Associated with genitals [TOS]

2.5—pain relief, relaxation [MB]; production of endogenous opiates. [EQ]; Use for sedative effect [ESP]; Sedative effect—reported use on bleeding, bruises, insomnia, and sinusitis. [RS] Sexual stimulation? [SX]

2.57 Associated with bladder [TOS]

2.67 Associated with intestines [TOS]

3.0-5.5—"Theta1" Range. [DW]

[DW] divides the Theta Range into Theta1 & Theta2.

3.0 Increased Reaction Time [RT] [SS]; 3.0 HZ & below used to reduce muscle tension headaches, but worked less well on migraines & sinus headaches. [RED]; used to treat allergies, in conjunction with 330 HZ [RS]

3.07 Associated with hara (3 cm or 1.5 inch below navel, balance of pelvis) [TOS]

3-4 Influences physical vision [SS]

3-6 Childhood awareness/vivid memories [SS+RA]

3-8 Theta Range according to [NEU]; deep relaxation, meditation, increased memory, focus, creativity, lucid dreaming, hypnagogic state [NEU]

3.4—Sound sleep 3.5—Feeling of unity with everything, accelerated language retention [×]; enhancement of receptivity [MB]; Earth Resonance (?) [SS]; (a remedy for) depression & anxiety [ESR]; Wholebeing regeneration, DNA stimulation [EH-d] [MPT] I was under the impression the Earth Resonance is 7.83 HZ—unless [SS] is talking about a different earth resonance.

3.5-7.5—Theta Range [per CRI]—Creativity, intuition, daydreaming, fantasizing, recollection, imagery, dreamlike, switching thoughts, drowsiness; "oneness", "knowing", repository for memories, emotions, sensations. Can lead to trance-like states. Theta strong during internal focus, meditation, prayer+spiritual awareness. Reflects state between wakefulness+sleep. Relates to subconscious. Observed in anxiety, behavioral activation+behavioral inhibition. Promotes learning+memory when functioning normally. (I think they mean it helps you process what you've learned—if you tried to actively learn while in the theta state, I doubt you'd have success—but sometimes the theta state can give your subconscious a chance to chew the proverbial fat that you've learned during the day, and digest it.) Abnormal in awake adults, but seen in children up to 13 years old. Suppression of theta can help concentration/focus of attention. [CRI]

3.6 (a remedy for) anger & irritability [ESR]

3.84 Associated with ovaries (Effects=vitality, life at every level) [TOS]

3.9 (a remedy for) unsociable behavior [ESR]; Theta/Delta brainwave range—crystal clear meditation, lucid dreams, enhanced inner awareness, "facilitates easy access to inner resources & creates space for inner peace+self-renewal". [SED]

4-6—attitude & behavior change [MH]

4-7—Theta Rang: recall, fantasy, imagery, creativity, planning, dreaming, switching thoughts, Zen meditation, drowsiness; Access to subconscious images, deep meditation, reduced blood pressure, said to cure addictions [SS]; Reset the brain's sodium potassium levels, which cuts down on mental fatigue [INT]; Increases sex drive [INT]; Meditation, Intuitive Augmentation [NEU]; Near Sleep brainwaves, conducive to profound inner peace, "mystical truths", transforming unconsciously held limiting beliefs, physical & emotional healing, purpose of life exploration, inner wisdom, faith, meditation, some psychic abilities, & retrieving unconscious material. [PWB]; bursts of inspiration, twilight sleep learning, deep relaxation, reverie, high levels of awareness, vivid mental imagery. Hypnopompic & Hypnagogic states [NSS via DW]; Military remote viewers operate in this range [RVX]

Some disagreement over the theta range—[NEU] lists it as 3.0 to 8.0 HZ. [AWI] lists it as 4.0 to 8.0 HZ. [RA] & [PWB] both have it as 4.0 to 7.0. [DW] divides it into two ranges, Theta1 (3.0-5.5 hz) & Theta2 (5.5-8.0 hz).

4.0-8.0 HZ Theta State according to [AWI]+[VUG via DW]—present in dreaming sleep, deep meditation, storehouse of creative inspiration, spiritual connection, subconscious mind [AWI]; creative insight, twilight ("sleep") learning, vivid mental imagery. Found in advanced meditators [VUG via DW]

4-12 Skeletal muscle resonances [SS]

4.0—Enkephalins, Extrasensory perception [MB]; Astral Projection, Telepathy, "Seduction mindset" [EI-d]; Catecholamines, vital for memory & learning, respond at around 4 HZ. [PSI]; Subconscious Problem Solving/Full Memory Scanning (if one can manage to stay awake) [RA+CAV via DW]; Associated with object naming, an important aspect of memory [TDM via DW]; "Those who suffer from Chronic Fatigue exhaust very easily. When moved to 4 HZ these individuals showed marked improvement in the length of time between the occurrence of exhaustion after certain exercises were completed." [NYT via NEU]

4.11 Associated with kidneys (Effects=strength) [TOS]

4.5 Shamanic State Of Consciousness/Tibetan Buddhist Chants [MMF via DW]

4.5-6.5 Wakeful dreaming, vivid images [SS]

4.6 Associated with spleen & blood (Effects=Emotional Impulse) [TOS]

4.9—Introspection [SS]; Induce relaxation, meditation, & deeper sleep [ESR]

5.0—unusual problem solving [×] reduced sleep needed, theta sounds replacing need for extensive dreaming [INT]; relaxed states, pain-relief (beta endorphin increases of 10-50% reported) [INT]; Alleged Sphincter Resonance (mechanical) (not good) [TB]

5.0-10.0 Relaxation [NEU]

5.14 Associated with stomach (Effects=Emotional Acceptance) [TOS]

5.35 Associated with lungs (Effects=Oxygen, Heat) [TOS]

5.5-8.0 "Theta2" frequency range: . . . Consists of trains (long runs) of rhythmic frontal activity centering at 6.5-Hz with amplitudes reaching the 50-100 uV (micro-volt) range . . . . Is induced in some people by the performance of a mental task such as mental arithmetic, tracing a maze, counting the number of cubes piled in a three-dimensional representation, & imaging a scene . . . . More common in extroverts with low traits of neurosis & anxiety. Because Theta2 is associated with mental tasks & its influence is seen in evoked potential latencies, Mizuki (1987) believes that the appearance of Theta2 closely relates to mechanisms of attention or arousal. [DW]

5.5—Moves beyond knowledge to knowing, shows vision of growth needed; "Inner Guidance" [SS]; Inner Guidance, intuition, heat generation [EI-d]

5.8 (reduce) Fear, Absent-mindedness, Dizziness [ESR]

6.0—long term memory stimulation [MB]; (reduce) unwillingness to work [ESR]

6.0-10.0 Creative Visualization—about 6 hz for a while, then up to 10 hz [NEU]

6-9.6 Somatic Responses, tingling, pressure, heat [SS]

6.15 Associated with heart (Effects=love,warmth) [TOS]

6.2-6.7 Frontal Midline Theta (Fm Theta) is a specific EEG frequency seen in those subjects actively engaged in cognitive activity, such as solving math problems & playing Tetris [TDM via DW]

6.26-6.6 Hemispheric desync, confusion, anxiety, low Reaction Time, depression insomnia [SS]

6.30 Hz—Mental & astral projection [SS seconded this]; accelerated learning & increased memory retention.[??]; (reduce) Anger+Irritability [ESR]

6.5—"Center" of Theta2 Brainwave Frequency Range [DW]; "Your frontal lobe, or brain entrainment of the two hemispheres is around 6.5 hz." [RA]

I quoted the second entry from [RA] directly, due to its ambiguity. It probably ties into what the 5.5-8.0 HZ entry says above.

6.8 Possible use for muscle spasms [ESR]; associated with telepathy/Schumann Resonance [DHA]

[DHA] associated 6.8 HZ with the Schumann Resonance and the Alpha-Theta borderline. I think this is slightly off—most sources consider the lowest frequency of the Schumann Resonance to be 7.83 HZ, and that's also considered the borderline between Theta brainwave and Alpha brainwaves.

6.88 Associated with collarbones (Effects=vitality, overall balance, stability) [TOS]

7.0-8.0 For healing purposes, like laying of hands by a healer, or self vizualization in a healing situation [RA]; Treatment of Addictions [DW]

7.0—Mental & astral projection, bending objects, psychic surgery; Increased Reaction Time [SS]; Mass aggregate frequency (can deaggregate matter), alleged to resonate & rupture organs at excessive intensity [TB]; Treatment of sleep disturbances [PGS via DW]; Bone growth [NOR]

7.5—Inter-awareness of self & purpose; guided meditation; creative thought for art, invention music, etc.; contact with spirit guides for direction; entry into meditation [MB]; At 7.5 HZ subjects who before suffered from confused thinking reported an ease at finding solutions to troublesome problems after a re-evaluation was conducted. [NYT via NEU]; Earth magnetic field frequency, useful theta (brain) waves frequency [TB]

7.5-8 For Treating Alcohol+Drug Addiction—This range of frequencies tells a person they're satisfied, which is "missing" in addictive personalities [RA]

7.69 Associated with shoulders (Effects=strength of the arms, expansion, teaching) [TOS]

7.8 Schumann Resonance (see 7.83 HZ), ESP activation [EI-d]; Doyere's group (1993), found that short high frequency bursts at 7.7 Hz induced LTP in prefrontal cortex, though only for one day. [AA via DW]

7.8-8 Stimulates ESP, paranormal [SS]

7.83—Earth Resonance, grounding [×], "Schumann Resonance." [TS, ESR+HSW, MAG]; anti-jetlag, anti-mind control, improved stress tolerance [SS]; psychic healing experiments [ESR]; pituitary stimulation to release growth hormone (helps develop muscle, recover from injuries, rejuvenation effects) [HSW]; Earth Resonance Frequency—'leaves you feeling revitalized like you've spent a day in the country.' [PWM via DW]; reports of accelerated healing/enhanced learning—"the earth's natural brainwave" [MAG]

[HSW] notes that higher octaves of the 7.83 Schumann Resonance can also stimulate the pituitary in the same way that 7.83 HZ can—especially 31.32 HZ. (One needs to be careful to distinguish between octaves of the 7.83 Schumann Resonance, and the other six Schumann Resonances, which are not higher octaves of 7.83 HZ.)

8-8.6 Reduced Stress/Anxiety [SS]

8.0-10.0 learning new information [MH]; Alpha—Rapid Refreshment 15 min [NEU]; "LOW ALPHA" inner-awareness of self, mind/body integration, balance [CRI]

8.0-12.0—Alpha range (per NEU, RA, PWM, NSS & CRI)—light relaxation, "super learning", positive thinking [NEU]; Conducive to creative problem solving, accelerated learning, mood elevation, stress reduction, etc., characterized by intuitive insights, creative "juice", inspiration, motivation, daydreams etc. Relaxed, yet alert [PWM via DW]; Associated with calm, relaxed, unfocused (not concentrating), lucid mental states, dream sleep & pleasant drifting feelings or emotions. [NSS via DW]; promotes mental resourcefulness, aids in mental coordination, enhances relaxation, "Can move quickly+efficiently to accomplish whatever task is at hand.", feelings of "at ease"+calm, promotes good moods, a bridge between conscious+subconscious, alpha waves indicate a person is alert but not actively processing information, seen more in extroverts than introverts, seen during creative problem solving [CRI]

8-13—Alpha range—Non-drowsy but relaxed, tranquil state of consciousness, primarily with pleasant inward awareness; body/mind integration; Amplifies dowsing, empty-mind states, detachment, daydreams, mind/body integration. (can cause) epileptic seizures [SS];
Note: [NEU], [RA], [PWM], [NSS]+[CRI] consider the alpha range to be 8.0-12.0. [AWI] considers it 9.0-14.0. [VUG] has it as 9.0-13.0.
8-14—Qi Gong and infratonic Qi Gong machine [QG]
8.0—Past life regression [×]; More Lymphocytes, DNA repair (RAD-6) [SS]; Associated with Base/Muladhara chakra (Color=Red) (Body Parts=Adrenals, Spinal Column, Kidneys) (Effects=Physical energy, will to live) (Note=C) [OML]
8.22 Associated with mouth (Effects=speech, creativity) [TOS]
8.3—Pick up visual images of mental objects [??]; clairvoyance [SS]; "Monroe Focus 12?" [NEU]
8.6-9.8 Induces sleep, tingling sensations [SS]
9.0, 11.0, 16.0 [bad] documented calcium ion migration (brain tissue) [SS] There's some disagreement over whether these frequencies offer anything to fear when used for binaural beats.
9.0-13.0—Alpha Range (according to [VUG])—relaxed, not thinking about anything in particular, sometimes a pleasurable feeling of "floating". Often dominant in certain kinds of meditation, alpha waves have for the past twenty years been associated with calm, lucid mental states (the "alpha state"). They're also often detected during dream sleep. This pattern typically occurs in daydreaming, relaxed awareness, guided or focused imagery & smoothly rhythmic athletic activity. There's often a euphoric, effortless feeling of "flow" as the doer is absorbed in activity and subject+object are felt to be united. [VUG via DW]
9.0-14.0 Alpha range (according to [AWI])—Relaxed & detached awareness, visualization, sensory imagery, light reverie. Also, gateway to meditation—provides bridge between the conscious & subconscious mind. [AWI]
9.0—Awareness of causes of body imbalance & means for balance[×] Blind person phantom touch reading (somatosensory cortex) [RA]; Associated with Sacral/Svadhisthana chakra (Color=Orange) (Body Parts=Gonads, Reproductive System) (Effects=Relationships/Sexuality) (Note=D) [OML]
9.19 Associated with upper lip (Effects=emotions, conflict resolution) [TOS]
9.4 Major frequency used for prostate problems. [ESR]—Self-explanatory. =)
9.41—Pyramid frequency (outside) (I can't find a good definition of "Pyramid Frequency". Anybody?)
9.5-10—Center of Alpha. Range—The brain's scanning/idling frequency—indicating a brain standing by, waiting to "give way to beta should attention be required, or be the bridge, the gate, to Theta & Delta for drowsiness, sleep, and certain cognitive challenges. [DW]
He gives credit for the 'brain scanning' factoid to Eccles & Walter (1950).
9.6—Mean dominant frequency associated with earth's magnetic field [EQ]; Facial Toning [ESR]
9.8-10.6 Alertness [SS]
10—enhanced release of serotonin & mood elevator, universally beneficial, use to try effects of other mixes [MB]. Acts as an analgesic, safest frequency, especially for hangover & jet lag. [EQ] Meg Patterson used for nicotine withdrawal. [MB3] dominant alpha frequency, clarity, normalcy, anti-convulsant, circadian rhythm resync, activate kidneys, raise body temp, more serotonin [SS]; Good when trying to correlate information by the subconscious—Sort of a waiting frequency while the subconscious does the work at lower frequencies. [RA]; Motor impulse coordination (Motor Control cortex) [RA]; Learning a foreign language [RA+PWM via DW]; Centering, Sleep Spindles, Arousal [EI-d]; Associated with Solar Plexus/Manipura chakra (Color=Yellow) (Body Parts=Pancreas, Stomach, Liver, Gall Bladder, Nervous System) (Effects=Spiritual wisdom, self-healing) (Note=E) [OML]; Increased alertness (caused by an increase in norepinephrine+serotonin & a decrease in melatonin), sense of well being & decreased pain (caused by increase in beta-endorphins) [RED]; Adrenal Stimulant [RS]; Significant improvements in memory, reading & spelling are reported (in conjunction with 18 HZ) [RUS via DW]; Treatment for Attention Deficit Disorder/Hyperactivity [LUB via DW]; Treatment for closed head injury [HOF via DW]; 'Berger Rhythm' [BER via DW]; (used on) headaches [RS]; ligament healing [NOR]
10-12: HIGH ALPHA RANGE—centering, healing, mind/body connection [CRI]
10-14 Dream/sleep spindles [SS]
10.2 Catecholamines
10.3 Associated With Nasal Passages (Effects=breathing, taste) [TOS]
10.5—Frequency for healing of body, mind/body unity, firewalking [×]; potent stabilizer & stimulating for the immunity, valuable in convalescence. [MB] Relaxed alertness, contemplation, body healing, mind over matter [SS] Lowering Blood Pressure [RA+PWM via DW]; Associated with Heart/Anahata chakra (Color=Green) (Body Parts=Thymus, Heart, Blood, Circulatory System) (Effects=Love of Life, love of self&others) (Note=F) [OML]
10.6—Relaxed & alert
10.7 Associated with ears (Effects=hearing, formal concepts) [TOS]
11.0 (& Below)—Stress Reduction (DW)
11-14 Focused alertness [SS]
11.0 (used to) achieve "relaxed yet alert" states. [PWM]
11.5-14.5 An implication for neurotherapy is that if increased intelligence+mental efficiency is the objective, then a frequency band with a 13-Hz center should be used. A more desirable frequency band than 12 to 15-Hz is 11.5 to 14.5-Hz. [DW]
12.0—Centering, doorway to all other frequencies [×]; frequency of earth resonance (Hercules—a researcher); Centering, mental stability, transitional point, time seems faster [SS]; To stimulate mental clarity [ESR]; Associated with Throat/Vishuddha chakra (Color=Blue) (Body Parts=Thyroid, Lungs, Vocal Cords) (Effects=Expression/self in society) (Note=G) [OML]
12.0-36.0 Beta Range [per CRI]—dominant brainwave in alert/awake/anxious adults with their eyes open. Comes into play when "listening & thinking during analytical problem solving, judgment, decision making, processing information about the world around us." [CRI]
12.0-14.0 Learning Frequency—Good for absorbing information passively, when you plan to think about it later. [RA] [RA] distinguishes between active studying where you're processing information & passive studying where you're just trying to absorb information+plan to think about it later. For the former, he suggests 36 to 44 HZ.
12.0-15.0 Beta (low)—relaxed focus, improved attentive abilities [NEU+CRI]; Treating Hyperactivity [RA]; Sensorimotor Rhythm (SMR)—Used in the treatment of mild autism [AUT via DW]

12.3 Associated with eyes (Effects=Visualization) [TOS]

13-27—Beta Range (according to [NSS])—Associated with focused attention towards external stimuli, alert mental activity, normal waking consciousness, & active thought processes. [NSS via DW]

13-30—Beta Range—Normal wakefulness, the taking in & evaluating of various forms of data received through the senses. It's present with worry, anger, fear, hunger & surprise. [×] Waking state, motivation, outer awareness, survival, problem solving, arousal, dendrite growth, combats drowsiness [SS]; Conscious Thinking, Autonomic Processes & Emotions [EH]

[NSS] considers Beta to be 13-27 HZ, [AWI] considers it 14-38 HZ, [PWM] & [RA] consider it 13-40 HZ, and [VUG] (seems to) consider it 14-30 HZ. [CRI] lists it as either 12-36 or 14-36—it contradicts itself in different parts of the article. [NEU] breaks up Beta into ranges—Low Beta=12-15 HZ, Mid Beta=15-18 HZ, & High Beta=18.0+HZ. [CRI] does as well.

13-40 Beta Range (according to [RA]+[PWM])—a high frequency pattern, conducive to stimulating energy+action; most of our current institutionalized education is beta geared, characterized by logical, analytical, intellectual thinking, verbal communication, etc. [PWM via DW]

13.0—Alleged sphincter resonance (mechanical) (not good) [TB]; Associated with Brow/Ajna chakra (Color=Indigo/Violet) (Body Parts=Pituitary, Lower Brain, Left Eye, Ears, Nose, Nervous System) (Effects=Visualization, Conceptualization) (Note=A) [OML]

13.8—Associated with Frontal Lobes (Effects=the seventh sense, final decision) [TOS]

14-16—associated with sleep spindles on EEG during second stage of sleep [EQ] [note SS said 10-14]

14-15—Slows conditioned reflexes [SS]

14.0-30.0—Beta Range (VUG)—This pattern is optimal for intense mental activities such as calculations, linear logical analyses & other highly structured functions [VUG via DW]

14.0—Awake & alert [??]; Alert focusing, vitality, concentration on tasks [SS?]; Schumann Resonance (2nd of 7 frequencies. 7.83 HZ being the first) [TS+HSW]; Intelligence Enhancement in conjunction with 22.0 HZ (medium=audio-visual stimulation) [APE]

[APE] used audio-visual stimulation alternating between 14 & 22 HZ. Check the link under [APE]'s bibliography entry for more information.

14.1 "Earth Resonance" [SS]; Earth Harmonics—accelerated healing [EI-d] (probably tied to Schumann Resonance above.)

15.0-18.0 Beta (mid)—increased mental ability, focus, alertness, IQ [NEU+CRI]; "alert but not agitated"/"aware of self & surroundings" [CRI]

15-24 Euphoria [SS][MPT]

15—chronic pain [MB]; Sound which bypasses the ears for sublimination (auditory cortex) [RA]; Associated with Crown/Sahasrara chakra (Color=Violet/White) (Body Parts=Pineal, Upper Brain, Right Eye) (Effects=Integration of personality & spirituality.) (Note=B) [OML]; capillary formation, fibroblast proliferation, decreased skin necrosis [NOR]

15.4—Associated with Cortex (Effects=intelligence) [TOS]

16.0—bottom limit of normal hearing [MP2]; Release oxygen & calcium into cells [CC]

16.4 Associated with top of head (Effects=spirit, liberation, transcendence) [TOS]

18.0-22.0—Beta: outward awareness, sensory data [??]; Throws brain's sodium/potassium levels out of balance, resulting in mental fatigue. [INT]; Theoretically can be used to achieve a "relaxed body/focus mind" state of consciousness [DW]

[INT]+[DW] seem to contradict each other here.

18.0+Beta (high)—fully awake, normal state of alertness, stress & anxiety [NEU]; Significant improvements in memory, reading & spelling are reported (in conjunction with 10 HZ) [RUS via DW]; (used to) improve hyperactive behavior [PWM via DW]; Associated with mental activity like math+planning—alert, but may also be agitated [CRI]

20-30 Phospene imagery, peak luminosity in visual field [SS]

20-40 Meditation For Stress Relief/Just At The Edge Of Audible Sound/As A Musical Background [RA]

20.0—fatigue, energize. Causes distress during labor. [EQ]; Human Hearing Threshold [SS]; Schumann Resonance (3rd frequency of 7) [TS+HSW]; Imposing subconscious commands on another (thought center) [RA]; Stimulation of pineal gland [ESR] [JB]; Helps with tinnitus (a condition that causes ear-ringing) [JB]; Adrenal Stimulant, (used on) sinus disorders/sinus infection/head cold/headache [RS]; Commonly used "cure-all" Rife Frequency [CR]

20.215 LSD-25 [PSI] (he implies it could mimic the effects of)

20.3 "Earth Resonance" [SS]

Probably the same thing as the Schumann Resonance at 20 HZ.

22.0 Used in conjunction with 14 HZ for intelligence enhancement (medium=audio-visual stimulation)[APE]; Used in conjunction with 40 HZ for 'out of body' travel [EWI via DW]; Also used with 40 HZ for psychic healing. [FAH via DW] [APE] used audio-visual stimulation alternating between 14 and 22 HZ. Check the link under [APE]'s bibliography entry for more information.

22.027 Serotonin [PSI] (he's unclear what he means by this)

25.0 Bypassing the eyes for images imprinting (visual cortex) [RA]; Tested clinically with patients who complain of anxiety [PGS via DW]

26.0 Schumann Resonance (4th frequency of 7) [TS+HSW];

26.0-28.0 Astral Projection/produced during meditation by some [ANO]

26.4 "Earth Resonance" [SS]

27-44 Frequency range that cats purr at—said to have restorative effects on the body, particularly the 'healing and strengthening of bones' [BON]

27.5 lowest note on a piano [MP2]

30 Meg Patterson used for marijuana. [MB3]

30-60 Gamma Range—little known but includes decision making in a fear situation, muscle tension, [EH]

[INT] considers Gamma to start at 40 HZ.

30-190 Lumbago [AT]

30-500 High Beta: Some effects have been observed, [EH] considers 30 to be the beginning of the Gamma range, which it believes run to 60. It then considers 60 to 120 to be the Lambda range.

Incidentally, [INT] believes that 40 is where Beta ends & Gamma begins.

31.32 Pituitary stimulation to release growth hormone (helps develop muscle, recover from injuries, rejuvenation effects) (this is a higher octave of the 7.83 HZ Schumann Resonance) [HSW]

32 Desensitizer; enhanced vigour & alertness [MB]
33 Christ consciousness, hypersensitivity, Pyramid frequency (inside); Resonance (5th frequency of 7) [TS]
35-150 Fractures [AT]
35-193 Arthralgy [AT]
35 Awakening of mid-chakras, balance of chakras
36-44 Learning Frequencies, When [Actively] Studying Or Thinking Helps To Maintain Alertness. Waking Operating State [RA]; Frequencies of the olfactory bulb, prepiriform cortex & amygdala [DSH via DW]; Coordinates simultaneous processing of information in different areas of the brain. Associated with high-level information processing. 'A good memory is associated with well-regulated & efficient 40 HZ activity, whereas a 40 HZ deficiency creates learning disabilities.'[CRI]
38 Endorphin release [WL]
39.0 Schumann Resonance [6th frequency of 7] [TS]
40-60 anxiolytic effects & stimulates release of beta-endorphines [MB]
43-193 Carcinomatosis [AT]
40.0—dominant when problem solving in fearful situations. [EQ]; Gamma—associated with information-rich task processing & high-level information processing [NEU]; "'For scientists who study the human brain, even its simplest act of perception is an event of astonishing intricacy. 40 Hz brain activity may be a kind of binding mechanism', said Dr. Rodolfo Llinas a professor of neuroscience at New York University. Llinas believes that the 40-cycle-per-second wave serves to connect structures in the cortex where advanced information processing occurs, and the thalamus, a lower brain region where complex relay & integrative functions are carried out." [NME via NEU]; Used in conjunction with 22 HZ for 'out of body' travel [EWI via DW]; Also used with 22 HZ for psychic healing. [FAH via DW]; "40-Hz activity varies from 38.8 to 40.1-Hz, regardless of the electrode site. The average frequency is in the ~39.5-Hz range. In summary, when the body is profoundly relaxed & the mind is in a state of high focus and concentration, 20 & 40-Hz brain activity can be seen in the raw and quantitative EEG of some subjects. It is possible that 18 to 22-Hz Beta & possibly 40-Hz neurofeedback training may help create a "relaxed body/focused mind" state of consciousness." [DW]; Activity in the ectosylvian & lateral cortex, medial geniculate, reticular formation, center median thalamus & hippocampus [ROW via DW]; Confirming Sheer et al.'s work, compared the EEG of middle- & high-I.Q. subjects during mental multiplication activity. A 40-Hz rhythm occurred just prior to the subject's answering the question. Forty-Hz pulses are thought to lead to synchronization+coordination of neurons assigned to the processing of incoming sensory stimulation. Put in "computerese," 40-Hz may be the brain's "operating system" frequency [GIA via DW] Involved In The Processing Of Psi Information (see note) [EMC] Considered the dividing point between beta waves+gamma waves, although there's some disagreement about this. [INT]
45.0 Schumann Resonance (7th frequency of 7)[TS]
46.98—Useful for "weird effects" (use with 62.64 HZ and 70.47 HZ) [TB][TB]
50-60 Documented negative effects too numerous to mention There is no correlation given with signal strength or modality used, i.e. audio-visual, EMF, magnetic, electrostatic, gravitic. Also, most ELF research is now Govt classified, particularly since the mid-1960's when Hamer discovered behavioral effects as the result of applied sinusoidal field gradients as low as 4 volts. [SS via DW]
50.0—dominant frequency of polyphasic muscle activity, mains electrical in U.K. [EQ]; Slower cerebral rhythms [??]
55.0—Tantric yoga; stimulates the kundalini. [×]
60-120 Lambda Range—Little known but includes central nervous system activity [EH]
60 electric power lines
62.64—Useful for "weird effects". (use with 46.98 HZ and 70.47 HZ) [TB]
63 Astral projection [×]
65.8 Associated with coccyx (small triangular bone at end of the spinal column) (higher octave of 2.06 HZ) [TOS]
70-9,000 Voice spectrum [MP1]
70 Mental & astral projection; Endorphin production/used with electroanalgesia. [VPL]
70.47 Useful for "weird effects". (use with 46.98 HZ and 62.64 HZ) [TB]
72 Emotional spectrum [??]; Used on sinusitis/sinus infection/head cold [RS]
73.6 Associated with genitals (higher octave of 2.30 HZ) [TOS]
80 Awareness & control of right direction. Appears to be involved in stimulating 5-hydroxytryptamine production, with 160 Hz. Combine with 2.5 Hz. [EQ]
82.3 Associated with bladder (higher octave of 2.57 HZ) [TOS]
83 Third eye opening for some people
85.5 Associated with intestines (higher octave of 2.67 HZ) [TOS]
90.0-111.0 Pleasure-producing beta-endorphins rise between these frequencies. [PSI]
In the MIDI scale, the notes that would fall in this range begin with F#3 and go up to A3. ["A3" being the fourth octave up—since there's an A0, and A1, A2 lower than it.] Playing the F#3 and the A3 as a chord seems to function as a good painkiller. An additional undertone in the alpha range of frequencies sometimes helps too. [Try adding a tone around 12.5 HZ].
90.0 Good feelings, security, well-being, balancing [??]
95.0-125.0 Acoustical Resonances of Assorted Ancient Structures [ACS via DW]
95.0 Use for pain along with 3040 HZ [ESR]
98.4 Associated with hara (3 cm or 1.5 inch below navel, balance of pelvis) (higher octave of 3.07 HZ) [TOS]
100 Can help with pain [used with electrical stimulation] [CMP]
The site specifically mentions it can be good for pain initially, but then recommends using 0.5 or 1.5 to treat pain.
105 Overall view of complete situation
108 Total knowing
110.0 Frequency associated with stomach. [Note=A] [BH1] [BH4]; Associated with ovaries (Effects=vitality, life at very level) (higher octave of 3.84 HZ) [TOS]
111 Beta endorphins [MB2]. cell regeneration [??]
117.3 Frequency associated with Pancreas [Note=C#] [BH1] [BH4]
120-500 P.S.I., moving of objects, changing matter, transmutation, psychokinesis
120 Helps with fatigue (Medium=pad)[JB]; (used on) sinus disorders/sinus infection/head cold [RS]
125 Graham potentializer; Stimulation [MH]; (used on) sinusitis [RS]
126.22—Sun, 32nd octave of Earth year [HC]; The Frequency Of The Sun (Note=C) (Color=Green) (Tempo=118.3 BPM) (Chakra=Manipura, also called Hara {associated with Navel & 3rd lumbar vertebrae}) (Effects=advances the feeling of centering of magic & of the transcendental) [HC/Planetware website]
There seems to be a little disagreement between [HC] & [HC/Planetware] over what exactly this is the frequency of—

[HC] ties this into the period it takes the earth to revolve around the sun, while [HC/Planetware] says this is the frequency it would take an imaginary planet to orbit the outside edge of the sun. There is another frequency that is given for the Earth year. (136.1 HZ)

132.0 Associated with kidneys (Effects=strength) (higher octave of 4.11 HZ) [TOS]; Associated with coccyx (small triangular bone at end of the spinal column) (higher octave of 2.06 HZ) [TOS]

136.1 Sun: light, warmth, joy, animus [RV]; Resonates with the earth year (Note=C#) (Color=Turquoise Green) (Effects=calming, meditative, relaxing, centering) [PSI]; Period it takes earth to revolve around sun (Tempo=63.8*127.6) (Chakra=Anahate/Heart chakra) (Effects=relaxing, soothing, balancing, harmony with the cosmos, associated with the soul {"frequency of the soul"}) (Medicinal=Sedative) (Other=significant tone in Indian music {called it the "sadja" or "father to others"—it was a keynote}—corresponds to "OM" & the Christian "AMEN") [HC/Planetware website]

140.25 Pluto: power, crisis & changes [??]; Frequency associated with the orbit of Pluto; (Note=C#) (Color=blue-green) (Tempo=65.7*131.4 BPM) (Effects=support the magic group dynamic principle and is said to be responsible for integration into certain structures of society) [HC/Planetware website]

141.27 Mercury: intellectuality, mobility [??]; Frequency associated with orbit of Mercury (Note=C# or D) (Color=blue-green or blue) (Tempo=66.2) (Chakra=Vishudda/Throat chakra) (Effects=Supports speech center and communicative-intellectual principle, associated with communication and cleverness) [HC/Planetware]

[HC/Planetware] says the frequencies of planets revolving around the sun are less important than those of the moon, sun, and Earth.

Again, I'm not sure how [HC/planetware] is associating these frequencies with these chakras. {shrugs}

A discrepancy in the note and color—they're both given twice—once as C# and blue-green, the second time as D and blue.

[HC/Planetware] and [BH] seem to associate different frequencies with the revolutions of each planet—these frequencies are determined by HC/Planetware by taking higher octaves of the actual period—octaves that are in the audible range. [BH] might use even higher octaves than [HC/Planetware] does, or some other method completely.

144.0 (helps with) headaches (Medium=pad)[JB]

144.72 Mars: activity, energy, freedom, humor [??]; Frequency associated with the orbit of Mars (Note=D) (Color=blue) (Tempo=67.8*135.6 BPM) (Effect: Supports strength of will and focused energy, ability for achievement) [HC/Planetware]

146.0 (used on) sinus infection/head cold [RS]

147.0 Associated with the spleen/blood (Effects=Emotional Impulse) (higher octave of 4.6 HZ) [TOS]; Associated with genitals (higher octave of 2.30 HZ) [TOS]

147.85 Saturn: separation, sorrow, death [??]; Frequency associated with orbit of Saturn (Note=D) (Color=Blue) (Tempo=69.3*138.6 BPM) (Effects=enhances concentration and the process of becoming conscious+shows very clearly karmic connections, brings structure and order—is considered to be a cosmic controller) [HC/Planetware]

I'm not completely sure what the dual tempo means. I'll have to research that further.

160.0 Appears to be involved in stimulating 5-hydroxytryptamine production, with 80 Hz. [EQ]; Use for rapid relief from headaches [ESR]; used on sinus infection/head cold [RS]

164.3 Frequency associated with Gall Bladder [Note=E] [BH1][BH4]

165.0 Associated with stomach (Effects=Emotional Acceptance) (higher octave of 5.14 HZ) [TOS]; Associated with bladder (higher octave of 2.57 HZ) [TOS];

165.0-170.0 Spiritual fall/consciousness collapse [JM]

[JM] said to avoid between 165.0 HZ to 170 HZ, "although the repercussions extend for a ways on either side of that." He's not completely clear why he feels this particular range should be avoided. (He had said he'd go into more detail when Awakening Mind II is released.)

171.0 Associated with lungs (Effects=Oxygen, Heat) (higher octave of 5.35 HZ) [TOS]; Associated with intestines (higher octave of 2.67 HZ) [TOS]

172.06—Resonates with the Platonic year {about 26,000 years} (Note=F) (Color=purple-violet) (Effects joyful, cheerful, spiritual effect) [PSI]; The Frequency Of The Platonic Year (Color=red-violet {purple}) (Tempo=80.6 BPM) (Chakra=Sahasrara/Crown chakra) (Effects=cheerfulness, clarity of spirit, cosmic unity on highest levels) (Medicinal=antidepressive) (Other=F is considered the tone of the spirit, and had a lot of significance to the Chinese) [HC/Planetware website] Other sources [PM] disagree about the tone F being associated with the Crown chakra, which is how HC/Planetware connects this frequency to the crown chakra. [PM] considers the crown chakra to be associated with the B note, and not F.

176.0—Frequency associated with the colon. [Note=F or F#] [BH1][BH4]

183.58—Jupiter: growth, success, justice, spirituality [??]; Frequency associated with the orbit of Jupiter (Note=F#) (Color=Red) (Tempo=86.05*172.1 BPM) (Effects: supports creative power and continuous construction) (Associated with Jupiter: Generosity, Continuity, Magnanimity, Joviality) [HC/planetware website]

185.0—(used on) sinus infection/head cold [RS]

187.61 frequency of "moon culmination"; [HC/planetware website]

194.18 frequency of Synodic "Earth" Day {the "day tone"} (Note=G) (Color=Orange Red) (Tempo=91.0 BPM) (Chakra=Muladhar/Base chakra) (Effects=dynamic, vitalizing) (Medicinal="tonifies") (Other="weather determining" spheric frequency, influences proteins, brings one into harmony with nature") [HC/planetware website]

Note: By "weather determining", [HC/planetware] seems to imply that somebody tuned into this frequency may be able to predict the weather in the short-term future. I'm just a little, little bit skeptical of this one, but if anybody has any luck with it, let me know.

I'm not sure how [HC/planetware] is associating these chakras to these frequencies. It doesn't seem to be based on the note, since G isn't the note typically associated with the base chakra [per PM]. The associations might tie in with something astrological instead. {shrugs}.

194.71—Earth: stability, grounding [??]; Key Of G resonates with frequency of earth day, the color orange-red, & has a dynamic, stimulating, and energizing effect on the body-mind. [PSI]

There seems to be some disagreement between [PSI] and the original source for this list. [PSI] associates this frequency with energizing, while the original source associates it with stability/grounding.

I think this one, and the one right below it [197.71 HZ] might be based on the same thing. One source might have done a typo, and then other sources based their information from that.

197.0 Associated with heart (Effects=love,warmth) (higher octave of 6.15) [TOS]; Associated with hara (3 cm or 1.5 inch below navel, balance of pelvis) (higher octave of 3.07 HZ) [TOS]

197.71 frequency of Sideric Day; [HC/planetware website]

207.36—Uranus: spontaneity, independence, originality [??]; Frequency associated with orbit of Uranus {insert one of dozens of bad jokes here} (Note=G#) (Color=Orange) (Tempo=97.2 BMP) (Effects=supports the power of surprise and renewal, has primeval and erotic power) [HC/planetware website]

210.42 frequency of Synodic Moon (Note=G#) (Color=orange) (Tempo=98.6 BPM) (Chakra=Svadisthan {2nd Chakra}) (Effects=stimulates sexual energy, supports erotic communication) (Medicinal=regulation of menstruation, disturbances in the gland and lymph system) [HC/planetware website]

211.44—Neptune: the unconscious, secrets, imagination, spiritual love [??]; frequency associated with orbit of Neptune (Note=G#) (Color=orange) (Tempo=99.1 BPM) (Effects=supports intuition, the unconsciousness, and enhances the dream experience) [HC/planetware website]

220.0 Frequency associated with lungs. [Note=A] [BH1][BH4] Associated with collarbones (Effects=vitality, overall balance, stability) (higher octave of 6.88 HZ) [TOS]; Associated with ovaries (Effects=vitality, life at very level) (higher octave of
3.84 HZ) [TOS]

221.23—Venus: beauty, love, sexuality, sensuality, harmony [??]; Frequency associated with the orbit of Venus (Note=A) (Color=yellow-orange) (Tempo=103.7 BPM) (Chakra=Ajna/Third Eye) (Effects=supports higher love energy and aspiration for harmony) [HC/planetware website]

227.43 frequency of Sideric Moon; [HC/planetware website]

229.22 frequency of Metonic Cycle [related to moon]; [HC/planetware website]

234.16 frequency of Moon knot; [HC/planetware website]

241.56 frequency of Saros periode; [related to moon]; [HC/planetware website]

246.04 frequency of Apsidis rotation; [related to moon]; [HC/planetware website]

250.0 Elevate and revitalize 254.57 Frequency associated with orbit of Icarus (asteroid) [MPT]

256.0 Root Chakra (1:1) (Note=C) [BH3] [MWH]

263.0 Associated with mouth (Effects=speech, creativity) (higher octave of 8.22 HZ) [TOS]; Associated with kidneys (Effects=strength) (higher octave of 4.11 HZ)
[TOS]

264.0 Related to Personality somehow. (Note=C+) [BH4]

272.0 33rd octave of Earth year [HC]; Frequency associated with Selenium (mineral nutrient) (Note=C#) [BH]

272.2 Frequency associated with orbit of Earth (Note=C#) [BH2]

273.0 Transpersonal Chakra (1:15) [Note=C#] (Earth Orbit 272) [BH3]

280.5 Frequency associated with orbit of Pluto [Note=C#] [BH2]

281.0—Frequency associated with Intestines [Note=C#] [BH1]

281.6—Frequency associated with Small Intestine [Note=C#] [BH4]

282.4—Frequency associated with orbit of Mercury. [Note=D] [BH2]

288.0—Polarity Chakra (9:1) [Note=D] (Mars Orbit 289) [BH3]; Sacral Chakra [MWH]

289.4—Frequency associated with orbit of Mars. [Note=D] [BH2]

293.0—"unknown" Chakra (1:14) (Note=D+) (Saturn Orbit 296) [BH3]

I take it by D+, she means a note somewhere between D and D#. A quarter note, perhaps. [MPT]

294.0—Associated with the upper lip (Effects=emotions, conflict resolution) (higher octave of 9.19 HZ) [TOS]; Associated with the spleen/blood (Effects=Emotional Impulse) (higher octave of 4.6 HZ) [TOS]

295.7—Frequency associated with orbit of Saturn (Note=D#) [BH2]

295.8—Frequency associated with Fat Cells (Note=C#) [BH1][BH4]

296.07—Frequency associated with orbit of Toutatis (asteroid) [MPT]

304.0—Useful on headaches (medium=pad); sedation and pain relief (medium=tube) [JB+KFL]; (useful for) blood pressure, (and with) stiff muscles (KFL); Frequency associated with Potassium (mineral nutrient) (Note=D#) [BH]

310.7—Frequency associated with spin of Neptune (Note=Eb) [BH2]

315.0—Diaphragm Chakra (10:1) (Note=Eb) [BH3]

315.8—Frequency associated with Brain (Note=Eb) [BH1]

317.83—Frequency associated with Liver (Note=Eb) [BH1][BH4]

319.88—Frequency associated with Kidney (Note=Eb) [BH1][BH4]

320.0—Solar Plexus Chakra (10:1) (Note=Eb) [BH3] [MWH]; Frequency associated with Calcium (mineral nutrient) (Note=E or Eb) [BH]

321.9—Frequency associated with blood. (Note=E or Eb) [BH1][BH4]

324.0—Frequency associated with muscles. (Note=E) [BH1][BH4]

329.0 Associated With Nasal Passages (Effects=breathing, taste) (higher octave of
10.3 HZ) [TOS]; Associated with stomach (Effects=Emotional Acceptance) (higher octave of 5.14 HZ) [TOS]

330.0 Used to treat allergies in conjunction with 3 HZ [RS]

333.0 (used on) sinus infection/head cold [RS]

332.8—Frequency associated with orbit of Sun (Note=E) [BH2]

When [BH2] says the "orbit of the sun", I believe she means how long it would take an imaginary planet to orbit around the sun's outer boundary [circumference]. This is how [HC/planetware] made this calculation—the period is then lowered a few octaves to get it into the audible sound range. That's how [HC/planetware] does most of its calculations, and probably how [BH] does it as well. [HC/planetware], when lowering [or in the case of planets raising] the octave, seems to gun for lower tones than [BH] does. The [HC/planetware] tones would be a little "bassier". Which is probably why the frequencies of all these astronomical phenomena that [HC/planetware] gives doesn't line up with the frequencies that [BH] gives.

336.0—Frequency associated with Molybdenum (mineral nutrient) [BH]
341.0—Heart Chakra (1:12) (Note=F) [BH3] [MWH]
[MWH] had the Heart Chakra at 341.3, if you want to nitpick.
342.0—Associated with ears (Effects=hearing, formal concepts) (higher octave of 13.8 HZ) [TOS]; Associated with lungs (Effects=Oxygen, Heat) (higher octave of 5.35 HZ) [TOS]
352.0—Frequency associated with bladder. (Note=F) [BH1] [BH4]; Thymus Chakra (11:1) (Note=F#) [BH3]
There seems to be a discrepancy here as to which note this frequency is. [BH] cites both F and F#. [MPT]
360.0—The "Balance Frequency"—brings sensations of joy and healing/derived from the Golden Section/brings balance to health/(per NASA astronauts) the Earth creates a 360 HZ tone in space.) [EI]
367.0—(used on) sinus infection/head cold [RS]
367.2—Frequency associated with orbit of Jupiter (Note=F#) [BH2]
368.09—Frequency associated with orbit of Apollo (asteroid) [MPT]
372.0—"unknown" Chakra (1:11) (Note=G#) (Earth Spin 378) [BH3]
375.70—Frequency associated with the orbit of Eros (asteroid) [MPT]
378.5—Frequency associated with spin of Earth. (Note=F#) [BH2]
380.96—Frequency associated with orbit of Ida (asteroid) [MPT]
384.0—"Gurdjieff vibration associated with root chakra. Sixth harmonic of six, center of the brainwave spectrum." [RP]; Throat Chakra (12:1) (Note=G) [BH3][MWH]; Frequency associated with Chromium (mineral nutrient) (Note=G?) [BH]
389.4—Frequency associated with spin of Mars. (Note=G) [BH2]
393.0—Associated with eyes (Effects=Visualization) (higher octave of 12.3) [TOS]; Associated with heart (Effects=love, warmth) (higher octave of 6.15) [TOS]
393.34—Frequency associated with orbit of Pallas (asteroid) [MPT]
394.76—Frequency associated with orbit of Ceres (asteroid) [MPT]
396—G (musical note) [PL]; "Liberating Guilt and Fear"/Solfeggio Frequency 'UT'[SE]
400 Seems to decongest [KFL]; Frequency associated with Manganese (mineral nutrient) (Note=G or G#) [BH]
**405—Violet [PL]—(!!!) See Glossary entry "COLOR"
408.7—Frequency associated with orbit of Juno (asteroid) [MPT]
409.1—Frequency associated with spin of Venus (Note=G#) [BH2]
410.0—"unknown" Chakra (1:10) (Note=Ab) (Venus Spin 409) [BH3]
414.7—Frequency associated with orbit of Uranus (Note=G#) [BH2]
416.0—Psychic Center Chakra (13:1) (Note=Ab) (Uranus Orbit 415) [BH3]; Frequency associated with Iron (mineral nutrient) (Note=Ab) [BH]
417—"Undoing Situations and Facilitating Change"/Solfeggio Frequency 'Re' [SE]
418.3—Frequency associated with bones (Note=Ab) [BH1] [BH4]
420.82—Moon: love, sensitivity, creativity, femininity, anima
421.3—Frequency associated with orbit of moon (Note=Ab) [BH2]; Also associated with spin of Mercury, but here, she lists the Note as "A" [BH2].
422.8—Frequency associated with orbit of Neptune (Note=Ab) [BH2]
424.0—(used on) Fatigue (medium=pad) [JB]; Frequency associated with Iodine (mineral nutrient) (Note=Ab) [BH]
426.7—Brow Chakra (Note=A) [MWH]
[MWH] calls this A, but it's flatter than the A of Western Music at 440 HZ. One could justifiably call it Ab. It's probably closer to Ab than it is to A.
430.8—Frequency associated with spin of Uranus (Note=Ab) [BH2]
**438—Indigo [PL?] (!!!)—See Glossary entry "COLOR"
439.0—Crown Chakra (Note=A? B?) [MWH]
For the modern diatonic scale, this would be an A note. [MWH] calls it a B note on their website. I'm not sure if they're perhaps basing this on some older scale. The frequencies that notes exist at have changed over the years.
440—A (musical note) [PL?]; Associated with Frontal Lobes (Effects=the seventh sense, final decision) (higher octave of 13.8) [TOS]; Associated with collarbones (Effects=vitality, overall balance, stability) (higher octave of 6.88 HZ) [TOS]
441.0—The King's Chamber Frequency—acts towards preservation and equilibrium [EI]
Per [EI]'s website, "Play a 441 HZ tone in a chaotic room and people will find themselves mellowing down." I -dare- somebody to actually test this and see if it holds any water.
442.0—Frequency associated with orbit of Venus. (Note=A) [BH2]
448.0—Third Eye Chakra (14:1) (Note=A) [BH3]
445.0—["unknown"] Chakra (1:9) (Note=Bb) (Venus Orbit 442) [BH3] That's what [BH] put "unknown" [MPT]
455.4—Frequency associated with spin of Saturn (Note=A#) [BH2]
456.0—(used on) sinusitis/sinus infection/head cold [RS]
461.67—Frequency associated with orbit of Vesta (asteroid) [MPT]
464.0—Frequency associated with Copper (mineral nutrient) (Note=Bb) [BH]; (used on) sinus infections/head colds w/728 hz, 784 hz & 880 hz [RS]
**473—Blue [PL?] (!!!)—See Glossary entry "COLOR"
473.9—Frequency associated with spin of Jupiter (Note=Bb) [BH2]
480—Crown Chakra (15:1) (Note=B) [BH3]; Frequency associated with Phosphorous & Zinc (mineral nutrients) (Note=B) [BH]
486.2—Frequency associated with spin of Pluto (Note=B) [BH2]
492.0—Frequency associated with Spleen (Note=B) [BH4]; Associated with Cortex (Effects=intelligence) (higher octave of 15.4 HZ) [TOS]
492.8—Frequency associated with Adrenals (Note=B) [BH1]; Associated with Adrenals, Thyroid & Parathyroid [BH4]
493.00—Frequency associated with the orbit of Gaspra (asteroid) [MPT]
495—B (musical note) [PL?]
495.25—Frequency associated with orbit of Castalia (asteroid) [MPT]
497.1—Frequency associated with spin of Sun. (Note=B) [BH2]
500.0—(used to treat) Anthrax (medium=tube) [JB]
520.0—(used on) Headaches (medium=pad) [JB]
522.0—(used on) sinus infection/head cold [RS]

526—Associated with top of head (Effects=spirit, liberation, transcendence) (higher octave of 16.4 HZ) [TOS]; Associated with mouth (Effects=speech, creativity) (higher octave of 8.22 HZ) [TOS]
**527—Green [PL?]—(!!!) See Glossary Entry "COLOR"
528—C (musical note) [PL?]; "Transformation and Miracles (DNA Repair)"/Solfeggio Frequency 'MI' [SE]; "Used by genetic scientists to mend DNA/strengthens cell wall to boost immunity" [EI]
542—Bio-energetic frequency for Variolinum (i.e. smallpox vaccine). See disclaimer for 500 HZ. [RS]
569—Bio-energetic frequency for Variolinum (i.e. smallpox vaccine). See disclaimer for 500 HZ. [RS]
**580—Yellow [PL?]—(!!!) See Glossary Entry "COLOR"
586.0—Associated with Circulation & Sex (Note=C#) [BH4]
588.0—Associated with the upper lip (Effects=emotions, conflict resolution) (higher octave of 9.19 HZ)[TOS]
594—D (musical note) [PL?]
**597—Orange [PL?]—(!!!) See Glossary Entry "COLOR"
620—Keely Frequency (use with 630 and 12000) [TB]
630—Keely Frequency (use with 620 & 12000) [TB]
633—Bio-energetic frequency for Anthracinum (i.e. anthrax vaccine). See disclaimer for 500 HZ before even playing with this. [RS]
639—"Connecting/Relationships"/Solfeggio Frequency 'FA' [SE]
658—Associated With Nasal Passages (Effects=breathing, taste) (higher octave of 10.3 HZ) [TOS]
660—E (musical note) [PL?]
664—(used for) Fatigue (medium=pad) [JB]
685—Associated with ears (Effects=hearing, formal concepts) (higher octave of 13.8 HZ) [TOS]
**700—Red [PL?]—(!!!) See Glossary Entry "COLOR"
704—F (musical note) [PL?]
727 (used on) Allergies, Sinusitis [RS]; Commonly used "cure-all" Rife frequency [CR]
728—(used on) sinus infections/head colds w/784 hz, 880 hz & 464 hz. [RS]
741—"Awakening Intuition"/Solfeggio Frequency 'SOL' [SE]
784—(used on) sinus infections/head colds w/728 hz, 880 hz & 464 hz. [RS]
787—Associated with eyes (Effects=Visualization) (higher octave of 12.3) [TOS]; (used to treat) Allergies, Sinusitis [RS]; Commonly used "cure-all" Rife frequency [CR]
800—Commonly used "cure-all" Rife Frequency [CR]
802—(used on) sinusitis with 1550 HZ; (used on) sinus infection/head colds [RS]
820—(used on) sinus infection/head colds [RS]
832—Bio-energetic frequency for Variolinum (i.e. smallpox vaccine). See disclaimer for 500 HZ. [RS]
852—"Returning To Spiritual Order"/Solfeggio Frequency 'LA' [SE]
880—Associated with Frontal Lobes (Effects=the seventh sense, final decision) (higher octave of 13.8) [TOS]; (used on) Allergies, Sinusitis [RS]; (used on) sinus infections/head colds w/728 hz, 784 hz & 464 hz. [RS]; Commonly used "cure-all" Rife Frequency [CR]
952—(used on) sinus infection/head colds [RS]
965—Relaxes muscles, especially those of the neck [KFL]
984—Associated with Cortex (Effects=intelligence) (higher octave of 15.4) [TOS]
1000—Cerebral neurons
1052—Associated with top of head (Effects=spirit, liberation, transcendence) (higher octave of 16.4 HZ) [TOS]
1500—(used on) sinus infection/head colds [RS]
1550—(used on) sinusitis with 802 HZ, (used on) sinus infections/head colds [RS];
1552—(used on) eye disorders [KFL]
1600—(used on) eye disorders [ESR]
2025—Proton Precession/Water Resonance [TB]
2675—"The Crystal Resonator". A subharmonic of the frequency of quartz crystal. "extremely effective for charging and clearing quartz crystals . . . useful for clearing and balancing of their own energies. Some claim it energize crystals in the brain. Others say that it activates aspects of the auric field." (medium=sound/tuning fork) [JG]
3222—Bio-energetic frequency for Variolinum (i.e. smallpox vaccine). [RS]
3040—Use for pain along with 95 HZ [ESR]
4186—highest note on a piano [MP2]
4400—(used on) sinus infections/head colds—try scanning between 4384 & 4416 by intervals of 8 HZ. [RS]
5000-8000 HZ—recharge "brain batteries" most rapidly. Fastest recharge at 8000 HZ. "The anxiety-easing, memory-expanding 60-beat tempo creates easy communication with the subconscious mind." [PSI]
5000—Commonly used "cure-all" Rife frequency [TB+CR]; (used on) allergies, sinus infections/head colds—short use only—long exposures destroy red blood cells. [RS/KFL]
9999—General vitality & energy [KFL]
10,000—Commonly used "cure-all" Rife frequency [TB+CR]; (used to treat) alcoholism, allergies, headaches [RS]
12,000 HZ—Keely Frequency (use with 620 HZ & 630 HZ) [TB]
16,000-20,000—Upper range for normal hearing [MP2]
23,000 up—Hypersonic Sounds [above human hearing]
38000-40000 HZ—Magic Window [EX via MM+TB]
42800 HZ—Aetheric dissociation/water resonance (water→aetheric force) [TB]

BIBLIOGRAPHY

The sources for each of the above identified frequencies or frequency ranges are explained or derived from the references identified in the frequency listings as follows:
AA "Gates, States, Rhythms, and Resonances: The Scientific Basis of Neurofeedback Training", Andrew Abarbanel, Ph.D., M.D.
ACS "Acoustical Resonances of Assorted Ancient Structures", R. G. Jahn, P. Devereux, and M. Ibison (1996) "Rudimentary acoustical measurements performed inside six diverse Neolithic structures revealed that each sustained a strong resonance at a frequency between 95 and 120 Hz. Despite major differences in chamber shapes and sizes, the resonant modal patterns all featured strong antinodes at the outer walls, with appropriately configured nodes and antinodes interspersed toward the central source. In some cases, interior and exterior rock drawings resembled these acoustical patterns. Since the resonant frequencies are well within the adult male voice range, one may speculate that some forms of human chanting, enhanced by the cavity resonance, were invoked for ritual purposes."http://www.princeton.edu/~pear/Order_29.html
ANO Transcendental Meditation, Anthony Norvell, via email from bertei@yahoo.com.
APE Academic Performance Enhancement with Photic Stimulation and EDR Feedback, Thomas Budzynski, Ph.D, John Jordy, M.Ed. & others. Journal of Neurotherapy, http://www.snr-jnt.org/JournalNT/Vol3/JNT(3-3)2.htm AS AlphaStim (research survey)

AT Auriculotherapy device information from Bentek Corp. Earlobe type electrodes are specified for some conditions, TENS or ECG type electrodes for others. Device has two channels, indicated for each ailment.

AUT "Positive Outcome With Neurofeedback Treatment In a Case of Mild Autism", Arthur G. Sichel, Lester G. Fehmi, and David M. Goldstein http://www.snr-jnt.org/JournalNT/Vol3/JNT(1-1)8.html AWI The Anna Wise Center, http://www.annawise.com BAR BiologicalAgeReversor (Brainwave Generator preset), TheMind2 (alias), http://www.bwgen.com/presets/desc129.htm BER Hans Berger, German Psychiatrist, 1929

BON Bone-healing/Restorative "Purring Frequencies" (Brainwave Generator preset), Created by: weap0ner@aol.com, hap://www.bwgen.com/presets/desc186.htm BH Barbara Hero, http://members.aol.com/Lambdom3/Chakras.html—the data comes from the following tables on her site:

BH1 NOTES AND FREQUENCIES OF THE ORGANS OF THE BODY

BH2 ORBITS AND SPINS OF OUR PLANETS

BH3 CHAKRA ENERGY CENTERS OF OUR BODIES.

BH4 COMPARISON OF PARTS OF THE BODY BASED ON THE SPEED OF SOUND THROUGH EACH ORGAN TO THE ABOVE (1996). Barbara Hero CA Compleat Astrologer, Derek & Julia Parker for slower physiological rhythms.

CAV "Cavanagh" (1972) [DW] associates Cavanagh with research done regarding brainwave frequencies and memory. He didn't give much information about [CAV], though.

CC Robert Becker, MD quoted in the book "Cross Currents" by Jeremy P. Tarcher, Inc., Los Angeles, 1990 The book itself was referenced in this article: http://www.nexusmagazine.com/articles/DecloakingPathogens.html CMP Owner's Manual for the Alpha-Stim® 100 microcurrent stimulator brand of transcutaneous electrical nerve stimulator, Complementary Medical Products Ltd., http://reiddds.comfproducts/100oman.html CNS Epsilon, Gamma, Hyper-Gamma and Lambda Brainwave Activity and Ecstatic States Of Consciousness, Center for Neuroacoustic Research, (c) 1999. http://www.jeffthompson.com/articleepsitext.htm CR Crane List, via the compiled lists on Turf's Electroherbalism Page. These are Rife-style frequencies, intended to be generated through an electromagnetic means. See glossary entry for Rife for more information.

CRI Crossroads Institute, "Brainwaves and EEG—the language of the brain", http://www.crossroadsinstitute.org/eeg.html DHA "CHIN MUSIC: An Evolutionary States Of Consciousness Model Of Language", Dan Hawkmoon Alford, 9/88, http://www.enformy.com/dma-chin.htm DSH Daniel Sheer [psycho-physiologist]

DW—Re: [bwgen] Water sound effect after listening theta waves, Dennis Webber, Yahoo Groups!: BWGEN, Tue Jul. 24, 2001 2:55 pm, http://groups.yahoo.com/group/bwgen/message/2024

EH One Way To Improve Sleep, The Equinox Alternative [Etonhall], link://www.etonhall.com/hol4.htm EI Exceed International, http://www.xtrememind.com, James R Plazo EI-d Deep Mind IV (Brainwave Generator preset), James R Plazo (Exceed International) http://www.bwgen.com/presets/desc111.htm EMC "40 HZ Brain Activity, Consciousness, and PSI" http://groups.yahoo.com/group/bwgen/message/3668

EQ Octaves and windows, Equinox, April 88

ESR Table of ElectroSpectrum Rife Device Frequency Codes VS. Actual Frequency (in HZ) Output. Archived via the compiled lists on Turf's Electroherbalism Page.

EX Excalibur Briefing, Thomas E Bearden

EWI An unpublished work done by Dr. Edgar Wilson & students of the Monroe Institute who were attempting to have an out-of-body experience. He found that as the students moved out-of-the-body, their beta activity increased dramatically at T3 and/or T4 with the highest amplitudes appearing at 22 & 40-Hz. (John F. Gilbert, Ph.D. & Robert Moroney, D. A., CPPS.) http://www.snr-jnt.org/JournalNR/JNT(2-1)5.html FAH Dr. Steven Fahrion presented a paper a couple of years ago concerning his work with healers and reported much the same results (as EWI). Perhaps these papers will be published at some future date. (John F. Gilbert, Ph.D. and Robert Moroney, D. A., CPPS.) http://www.snr-jnt.org/JournalNT/JNT(2-1)5.html GIA Giannitrapani (1969)

HC Hans Cuosto, Cosmic Octave, Life Rhythm. More on the cosmic octave at Planetware website http://www.planetware.de/tone/table.html] The HC entries may be used with sound or possibly vibration—HC advocated using tuning forks on precise body parts.

HOF Hoffman, Stockdale, Hicks, & Schwaninger, 1995.

HSW How Sound Works On The Body, Mindtech, (c) 2001 deadlink://www.mindtech.co.uk Note: the article was posted elsewhere: http://www.crosswynd.com/encounters.htm INT Intelegen, Inc (website) http://brain.web-us.com/binaural.htm JB James Bare, ("Bare book") Archived via the compiled lists on Turf's Electroherbalism Page.

JG Jonathan Goldman, Sound Healing With Sound Healer Jonathan Goldman (website), http://www.healingsounds.com/.

JM James Mann [Enlightened Enterprises], Awakening Mind I: Creating Sound and Light Sessions on Advanced Programmable Mind Machines, 1996, excerpts from at http://marks.on.ufanet.ru/PSY/AVS5.HTM.

KFL Kinnaman, Kinnaman Frequency List And Possible Effects, Archived via the compiled lists on Turf's Electroherbalism Page.

LUB "ADD/ADHD"; Lubar, 1991.

MAG "Megabrain" (article name), Magical Blend Magazine, P.O. Box 11303, San Francisco, Calif. 94101, USA, Found at: http://www.chscene.ch/ccc/habi2/134_megabrain.html MB Megabrain Germany MB2=Megabrain Report, v1 #2; MB3=Megabrain Report #3, p. 19

MH Mind Expanding Machines: Can the GP Do for the Brain What Nautilus Does for the Body?, by Michael Hutchison, New Age Journal July/August 87 Graham potentializer not in production.

MM Micromercurial Maze [website] http://geocities.com/ResearchTriangle/2888/These frequencies mentioned are likely intended to be generated through electromagnetic means, rather than audio means.

MMF Melinda Mansfield—Researcher
MP1 Chant: The Healing Power of Voice and Ear, an interview with Alfred Tomatis, M.D., by Tim Wilson, in Music: Physician for Times to Come, an anthology by Don Campbell
MP2 Sonic Entrainment, by Jonathan S. Goldman, in Music: Physician for Times to Come, an anthology by Don Campbell
MPT This denotes the frequencies calculated for the revolutions of the various asteroids, risen to a high enough octave to be heard as a sound. The frequencies of the asteroids were generated using the following method:
Step 1) Find a table that gives the revolution times of the asteroids (most give them in years).
Step 2) Divide 1 by the number of years an asteroid takes to complete a revolution. (This will give you the fraction of a revolution it completes in one year.)
Step 3) Divide by 365 (fraction of revolution in one day). Then divide by 24 (fraction of revolution in one hour). Then divide by 60 (fraction of revolution in one minute). And divide by 60 again (fraction of revolution in one second).
Step 4) So, you're left with the amount of the revolution an asteroid completes in one second. Since this frequency is very small, you need to raise it until it's into the range of audible sound. Now, begin doubling the number—this raises its octave.
MWH Natural Healing—Sound Therapy, Miracle Wellness House (website)—http://www.miraclewellnesshouse.com/energy_3.html
One thing that should be established about their Chakra system is they actually have the chakras repeating up through the various octaves. Each of the octaves represent a particular level of connection to things. The octave included here is associated with the physical body, according to the website.
NEU Neural Frequency Association Listings, The Neuro Matrix site—http://www.futuredynamicadvantage.com/research/frequencies.html
NME "A New Theory of Consciousness", HEALTH/SCIENCE, New Mexican Apr. 7, 1995
NOR "Science Measures The Human Energy Field", Nature's Own Research Association [Jim and Nora Oschman], article posted on this website: http://www.reiki.org/reikinews/ScienceMeasures.htm.
NSS Neurosync Software
NYT New York Times Science Section, 1989
OML Chakra Reference Chart, http://OMLOGOS.COM
The chart seems to imply that higher octaves of those frequencies also are associated with the chakras mentioned, since it uses them in a musical context, saying that the Crown chakra is associated with the "musical series of B", for example.
PL Power of Limits (see Accords chart) for colors and notes. There's some dispute over whether the color frequencies are accurate. It was mentioned on the Brainwave Generator message board these were wavelength values, not frequencies, technically.
PGS "Sub-threshold 10-Hz Sound Suppresses EEG Theta: Clinical Application for the Potentiation of Neurotherapeutic Treatment of ADD/ADHD", Paul G. Swingle, Ph.D., C. Psych. http://www.snr-jnt.org/JournalNT/JNT(2-1)3.html
Color Therapy, Downtown Express Productions, LLC.
Peaceful Mind-Alternative Medicine And Therapies [website] http://www.peacefulmind.com/color_therapy.htm
PSI PsiliPharm, "5,000 HZ Frequencies To Boost Growth Of Plants", Cannibis.Com,
PWM "Playing With Your Mind", Patricia Chamberlain, Unlimited Human magazine. March 1993.
QG China Healthways Inst.
RA Brainwave Entrainment Frequencies, Ray Auxillon, Jun. 15, 1999. members.tripod.com/~speculation/brainwave.html*
RED The Rediscovery of Audio-Visual Entrainment, David Siever, C.E.T., (c) 1997, found chapter at: http://www.mindalive.com/2_0/ch6.pdf (updated link—MPT Aug. 29, 2004). The entry at 3 HZ was a reference to experiments conducted by Glen Solomon in the 80s using a device called a Dzidra Glass. This was a visual means of brainwave entrainment, rather than an audio means. The entry at 10 HZ was a reference to experiments conducted by Norman Shealy, who studied the effects of 10 HZ photic stimulation. (brainwave entrainment using pulsing lights rather than sound)
ROW Rowland (1968)
RP Astral Travel with Orgone Energy Machine, Ray A. Proper, Fry's Incredible Inquiry
RS Reid Smith, an assortment of frequency tables from various sources that RS compiled. Archived via the compiled lists on Turf's Electroherbalism Page. Those frequencies listed that were compiled by Reid Smith are Rife-style frequencies—see glossary entry for Rife.
RUS Russell And Carter in a blind study (need to research this one for more info.)
RV Primordial Tones: Meditation on the Archetypal Energies of Celestial Bodies, Joachim-Ernst Berendt, ReVision, Summer 1987 for planets.
RVX Remote Viewing: The Story Of The Real X-Files, Paranormal Management Systems, deadlink://www.fastnet.co.uk/pms/real_x.htm
SE "What Are The Ancient Solfeggio Frequencies?", SomaEnergetics.com, http://www.lightwithin.com/SomaEnergetics/2Solfeggio_Frequencies.htm
SED The Sedona Sound Experience (website), R. Brian Caldwell, http://www.metasonics.com/
SS Silent Sounds website—http://www.mindspring.com/~silent/menu.htm
SX "Re: Sexual Stimulation", posted on the Yahoo Groups Brainwave Generator message board by "R. Verhey" on Mar. 9, 2002. http://groups.yahoo.comigroup/bwgen/message/3315
TB Frequencies. ["interesting, useful, and weird frequencies"], Terry Bastian [tbastian@dmv.com], from a message in the Keely Net BBS Archives posted in July of 1998: http://www.keelynet.com/interact/Arc_7_98-12_98/00000221.htm
Again, the frequencies with this source listed are most likely intended to be generated through electromagnetic means.
TDM "Theta: Don't Tread on Me", Marvin Sams Ph.D., R.EEG T, QEEGT, L. Ac. http://www.snr-jnt.org/JournalNT/JNT(2-3)4.html
TOS Table Of Sound Frequencies Corresponding To The Human Body, http://lullianarts.net/body.htm. The compiler doesn't name himself on the page, but he gives his references, which are: Les Plans d'Expression, Marie-Louise Aucher, Paris, Mame, and: Revelatio Secretorum Artis, Ivo Salzinger, in Beati Raimundi Lulli Opera Omnia, Minerva, Mainz, 1975
TS Schumann Resonances, Geomagnetic Reversals, and Human Brain States, Tony Smith—web article at—http://www.innerx.net/personal/tsmith/Schumann.htm
VPL V. P. Lebedev (a Russian Researcher), studies from 1985-1990. (I got this source via M. Sandomirsky (marks@ufanetru) on the Brainwave Generator message board: http://groups.yahoo.com/group/bwgen/message/2552

VUG Voyager XL User Guide, 01993 Theta Technologies.

WL Wolfgang Ludwig

These are but some examples of frequencies believed through experience of various parties to have physiological or mood-enhancing effects when radiated as energy to a person. Many of these frequencies listed can be directly radiated as sound energy via a speaker, or as light energy such as via a video display by tailoring the refresh rate, change rate for a moving or cycling image. or other visible feature of the video image. Some frequencies are intended to be delivered as electromagnetic radiation, or as other energy directed toward the wagering game player.

Some embodiments will combine various methods of energy radiation, or will combine a mode of energy radiation with another feature such as presentation of a certain color believed to have a mood influence complementing the targeted result of the radiated energy frequency. Directly perceivable radiation such as sound or video in some embodiments will be superimposed or overlaid upon the normal multimedia presentation of the wagering game, and may not be directly noticed by the wagering game player. This serves to provide a mood-enhancing effect while not distracting the player from the wagering game at hand. Further, a tactile vibration device is attached in some embodiments to a radiating surface or to a stool or chair to reproduce certain portions of the frequency spectrum, including frequencies that are difficult, expensive, or distracting to radiate through the air via large speaker assemblies. Such assemblies also provide the benefit when attached to a chair or stool of efficiently and directly transferring vibration energy to the wagering game player rather than transmitting energy through the air in the general direction of a wagering game player.

When the energy presented to the wagering game player is designed to provide a relaxation response or to generate a feeling or mood of well-being, the wagering game player may realize mental and physical relaxation, lowered blood pressure, reduced heart rate, and lower breathing and metabolic rates. This results in a more enjoyable and less stressful gaming experience for the wagering game player, and can result in a wagering game player playing longer and enjoying the gaming experience to a greater degree.

Variation of the frequencies or in the direction or location of energy transmission is employed in some wagering game systems to prevent fatigue, and to address multiple physical, emotional, or physiological areas contributing to the mood of the wagering game player. In other embodiments, a range of frequencies is swept through, with further embodiments skipping over certain frequencies believed not to have a beneficial effect.

Another way in which transmission of energy by the mood enhancement module can be employed to enhance the wagering game player's mood and wagering game experience is to transmit electromagnetic radiation in the vicinity of the wagering game player's head or other parts of the central nervous system, at frequencies believed to influence the neural processes within the wagering game player. In one example, frequencies below 1 Hz are projected as sound and electromagnetic energy to the wagering game player, as discrete, complex, or modulated frequencies designed to address the mood of the wagering game player. In further embodiments, the magnetic field around the wagering game player's head, the wagering game player's speech, the wagering game player's skin conductance, or other biometric measurements are taken to employ biofeedback and to alter or control the presentation of energy to the wagering game systems.

Yet another method of transmitting energy under the control of a mood enhancement module to enhance the mood of a wagering game player comprises operation of an air ionizer to maintain a desired level of ions per unit of volume in the vicinity of the game player. In one example, the air is monitored, and the ionization is controlled to produce a level of 2,000 to 4,000 ions per cubic centimeter in the vicinity of the wagering game player. This charge level is typical of country air, an when the wagering game player breathes the air it results in enhancement of the wagering game player's mood as if the wagering game player were in the country breathing fresh country air.

The wagering game system of FIG. 4 is therefore able to improve the gaming experience for wagering game players by presentation of one or more mood enhancing energies via the various components of the mood enhancement module. Because people are capable of distinguishing large-scale and complex patterns, and remember feelings of well-being particularly well, such a system can enhance customer loyalty to those wagering games employing mood enhancement functionality and result in greater market share for the wagering game system manufacturer and a consistently more enjoyable gaming experience for the wagering game player.

Figure 5:
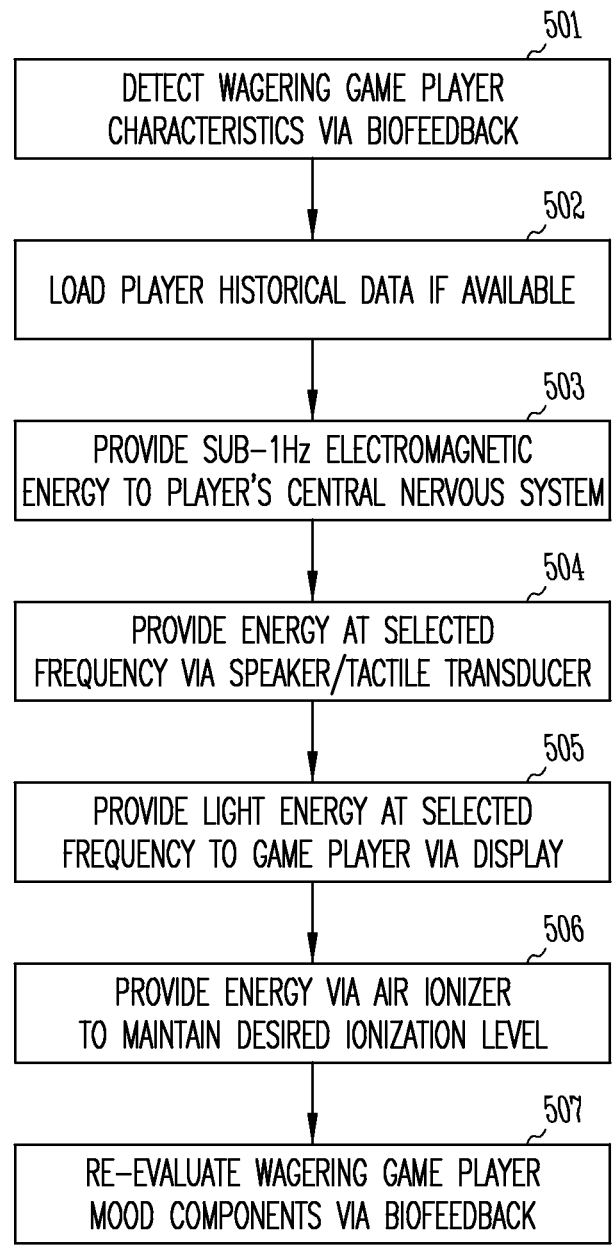
FIG. 5 is a flowchart showing an example method of operating a mood enhancement module in a wagering game system.

FIG. 5 is a flowchart, illustrating a method of practicing one example of the present invention. At 501, the mood enhancement module detects the wagering game player's characteristics via biofeedback. Biofeedback includes in various embodiments detection of a variety of physiological characteristics, such as pulse, skin resistance, respiration rate, vocal characteristics, or other such characteristics. In other embodiments, the wagering game player's mood-affecting characteristics are input via other inputs to the wagering game, such as by selecting from a variety of options on the touchscreen indicating the wagering game player's present mood characteristics.

In embodiments having a network connection, a central server can be employed to store historical data regarding a particular identified player's mood-related history. The player's historical data can them be loaded at 502, and is used to select the frequencies at which energy is provided to the wagering game player.

Energy is transmitted to the wagering game player in the form of electromagnetic radiation at 503. In some embodiments, the energy is at a level below 1 Hz, and is directed toward the player's central nervous system such as toward the wagering game player's brain. In further embodiments, the low frequency energy provided via the electromagnetic transducer is supplemented by low frequency audio energy provided as beats or difference tones, or is supplemented by a tactile transducer.

At 504, the wagering game system provides energy at a selected frequency via a speaker or a tactile transducer to produce vibration energy. Although the effective frequency of speakers is typically limited from the mid-double digit frequencies to about 20 kHz, frequencies lower than even the audible limit of about 20 Hz can be produced as beats when two or more fundamental tones within the speaker's range are produced. To further supplement low frequency energy, a tactile transducer is employed in some embodiments to vibrate a seating surface such as a chair or stool. In alternate embodiments, the tactile transducer vibrates some other surface in contact with the wagering game player, or vibrates a panel of the wagering game machine to produce low frequency vibrations that are conducted through air to the wagering game player.

At 505, light energy is provided to the wagering game player such as via the display, or via another light source such as a game sign or a secondary or top-box display. The frequency is provided in some embodiments by alteration of the refresh rate of the screen, by controlling the movement of an object on the screen, or by modulation of the backlight or other illumination power source for the display. In a further embodiment, the energy is presented such that it is not directly observable by the wagering game player, and so does not distract the player from game play, but is masked by the other video elements such as game play elements.

At 506, an air ionizer is employed to maintain air ionization at a desired level, such as that of an outdoor open space. This is estimated to be between 2000-4000 ions per cubic inch of space, or more generally 1000-5000 ions per cubic inch of space.

Biofeedback is again employed at 507, where the wagering game player's mood-affecting components are again evaluated to determine the wagering game player's physiological state. The process then returns to 503, and the various frequencies of energy are adjusted based on the physiological or biometric measurements. In a further embodiment, the frequencies of energy presented are also cycled or changed periodically to avoid causing fatigue in the wagering game player.

Figure 6:
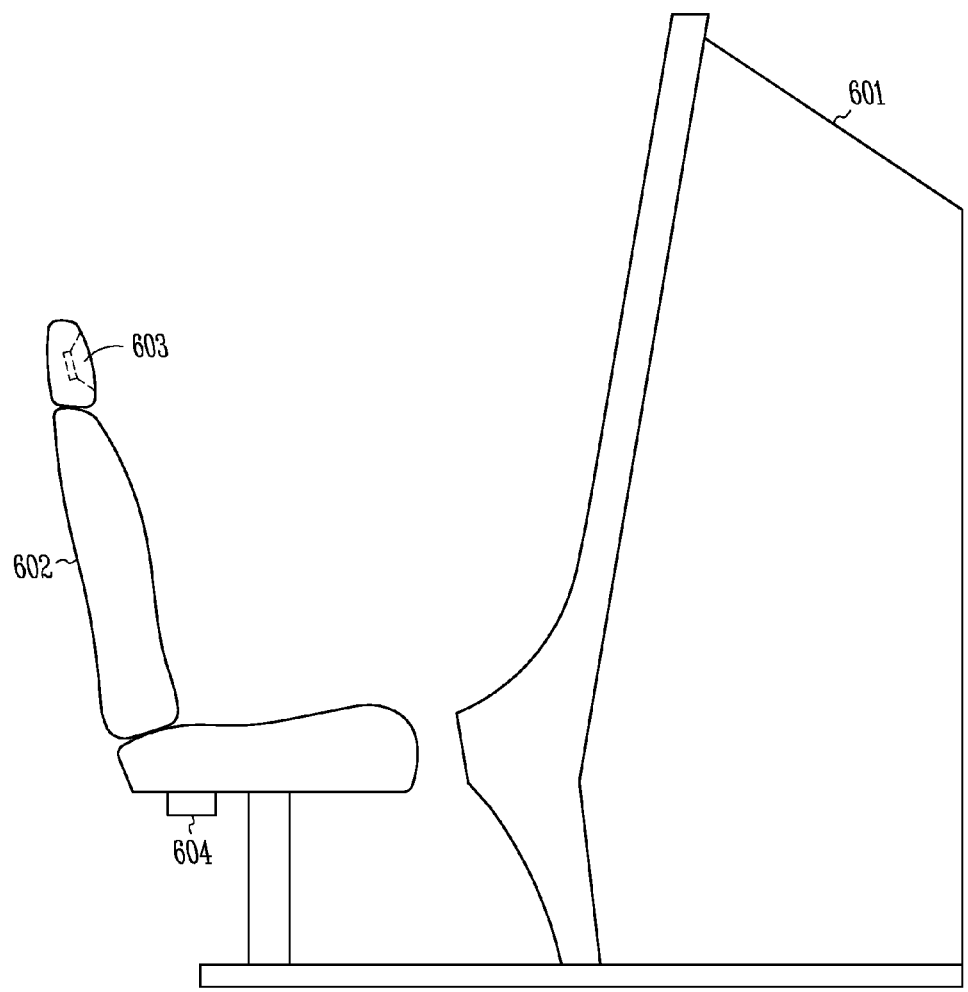
FIG. 6 shows a wagering game system comprising a chair having audio and tactile transducers coupled to a mood enhancement module, consistent with an example embodiment of the present invention.

FIG. 6 shows a configuration of a wagering game system employing a mood enhancement module operable to control a tactile transducer mounted to a seat that is a part of the wagering game system. The wagering game system 601 is mounted to a base that is coupled mechanically and via electrical connection to a seat 602, positioned in front of the wagering game machine in position for a wagering game player to play the wagering game while seated in the seat 602.

The seat further comprises one or more speakers 603, that are operable to play sound at the direction of the wagering game, such as via electrical connection to the wagering game machine's audio system 406 of FIG. 4. The speakers are in one embodiment operable to play sound as part of a surround-sound speaker configuration, and in another embodiment are operable to play frequencies at the direction of the mood enhancement module to provide acoustic energy to the wagering game player seated in the seat 602. Although speakers are typically limited in low-frequency response to frequencies above 20-50 Hz, depending on the speaker size and configuration, use of multiple higher frequencies can produce beat tones in the sub-20 Hz frequency range.

The seat also comprises a tactile transducer 604, coupled to a rigid frame element of the chair. The tactile transducer vibrates in response to an electrical signal, and transmits the vibrations through the rigid frame of the chair to the chair and to a wagering game player seated in the chair. The tactile transducer is able to directly produce vibration in the sub-20 Hz frequency range that the speakers 403 are often not able to directly produce, and so provide low frequency energy to the wagering game player more effectively than the speakers 603 alone. Because the vibration of the tactile transducer 604 is directly perceivable to the wagering game user's body when in contact with the seat 602, the tactile transducer also provides a massage effect in some embodiments.

The example embodiments of a wagering game machine having a mood enhancement module as presented here serve to illustrate how mood enhancement functionality can be employed in a wagering game system to address various elements such as physiological, emotional, and biological states that affect the mood of the wagering game player. By addressing these elements by transmission of energy at selected frequencies to the wagering game player, these elements can be influenced, resulting in a more enjoyable wagering game experience for the wagering game player. Other biometric feedback methods are presented in other examples, illustrating how biofeedback can be used in a wagering game system to provide a wagering game presentation that a game player finds more interesting and entertaining over a longer period of time. The game player will therefore have a more enjoyable game experience, and the owner or operator of the game will benefit from greater brand loyalty or sustained interest in a particular wagering game product. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the example embodiments of the invention described herein. It is intended that this invention be limited only by the claims, and the full scope of equivalents thereof.

The invention claimed is:

1. A method of operating a gaming system, the gaming system including one or more processors and an electronic gaming machine for conducting a wagering game, the electronic gaming machine having a gaming cabinet with one or more electronic input devices and one or more electronic display devices coupled to the gaming cabinet, the method comprising:

detecting, by at least one of the one or more electronic input devices of the electronic gaming machine, a physical item associated with a monetary value, the monetary value establishing a credit balance that changes based on play of the wagering game;

receiving, by at least one of the one or more electronic input devices of the electronic gaming machine, a wager input from a player to play the wagering game, the wager input being covered by the credit balance;

initiating, by at least one of the one or more processors, the wagering game in response to the wager input from the player;

determining, by at least one of the one or more processors of the gaming system, an outcome of the wagering game based, at least in part, on one or more random elements generated by at least one of one or more electronic random element generators;

collecting, via one or more biometric sensors operatively coupled to the electronic gaming machine, biofeedback data to determine a physiological state of the player during play of the wagering game;

loading a baseline biometric history of the player from stored historical data;

providing, by one or more electronic output devices of the electronic gaming machine, a selected frequency of energy to the player during play of the wagering game based on the loaded baseline biometric history;

evaluating, by the one or more processors, the collected biofeedback data to determine a new physiological state of the player;

adjusting the frequency of energy based on the evaluation; and receiving, by at least one of the one or more electronic input devices, a cashout input from the player to initiate a payout from the credit balance.

2. The method of claim 1, wherein evaluating the collected biofeedback data to determine the physiological state of the player comprises evaluating player body temperature, player blood pressure, player pupil dilation, player blood flow, or player pulse rate, or any combination thereof, measured by the one or more biometric sensors.

3. The method of claim 1, wherein providing a selected frequency of energy to the player comprises:
providing a selected frequency of light energy to the player via an electronic display device of the electronic gaming machine, wherein the selected frequency of light energy is provided by altering a refresh rate of the electronic display device.

4. The method of claim 1, wherein the selected frequency of energy comprises a selected frequency of sound energy provided by a speaker of the electronic gaming machine to supplement the vocal frequencies.

5. The method of claim 1, further comprising varying the frequency over time.

6. The method of claim 1, wherein loading the baseline biometric history from stored historical data comprises loading the baseline biometric history from a server via a network connection of the gaming system.

7. A wagering game system for conducting a wagering game, the wagering game system comprising:
an electronic gaming machine with one or more biometric sensors and one or more electronic output devices;
one or more processors;
one or more memory devices storing a gaming module and a biometric feedback module, the gaming module comprising gaming code executable by at least one of the one or more processors to present the wagering game to a user, the biometric feedback module comprising biofeedback code executable by at least one of the one or more processors to:
receive biofeedback data collected by at least one of the one ore more biometric sensors of the electronic gaming machine to determine the user's physiological state;
load a baseline biometric history of the user from stored historical data;
provide, by at least one of the one or more electronic output devices of the electronic gaming machine, a selected frequency of energy to the user based on the loaded baseline biometric history;
evaluate the collected biofeedback data to determine a new physiological state of the user; and
adjust the frequency of energy based on the evaluation.

8. The wagering game system of claim 7, wherein evaluating the collected biofeedback data to determine the user's physiological state comprises evaluating user body temperature, user blood pressure, user pupil dilation, user blood flow, or user pulse rate, or any combination thereof, measured by the one or more biometric sensors.

9. The wagering game system of claim 8, wherein the baseline biometric history comprises a time-averaged standard deviation indicating a normal degree of variability of a particular biometric measurement of the user during prior play of the wagering game.

10. The wagering game system of claim 8, wherein the energy comprises sound energy designed to supplement the user's vocal frequencies.

11. The wagering game system of claim 8, wherein the frequency of the provided energy is varied over time.

12. The wagering game system of claim 8, wherein the energy is provided to maintain a level of 1000 to 5000 ions per cubic centimeter in the vicinity of the user, including at least the user's head.

13. A gaming system for conducting a casino wagering game, the gaming system comprising:
an electronic gaming machine for playing the casino wagering game, the electronic gaming machine including a cabinet with one or more electronic input devices and one or more electronic display devices coupled to the cabinet, the one or more electronic display devices being configured to display aspects of the casino wagering game, the one or more electronic input devices including first and second input devices, the first input device being configured to detect a physical item associated with a monetary value that establishes a credit balance, the second input device being configured to receive a cashout input to initiate a payout from the credit balance, the credit balance changing based on play of the casino wagering game;
one or more biometric sensors; and
game logic circuitry comprising one or more processors and one or more memory devices storing instructions which, when executed by at least one of the one or more processors, cause the gaming system to:
receive by at least one of the one or more electronic input devices an input from a player to play the casino wagering game;
initiate the casino wagering game in response to the input from the player;
display on at least one of the one or more electronic display devices an outcome of the casino wagering game;
load a baseline biometric history of the player from stored historical data;
provide a selected frequency of energy to the player during play of the wagering game based on the loaded baseline biometric history;
collect, by at least one of the one or more biometric sensors, biofeedback data indicative of a physiological state of the player during play of the casino wagering game;
evaluate the collected biofeedback data to determine a new physiological state of the player; and
adjust the frequency of energy based on the evaluation.

14. The gaming system of claim 13, wherein the biofeedback data includes player body temperature, player blood pressure, player pupil dilation, player blood flow, or player pulse rate, or a combination thereof.

15. The gaming system of claim 13, wherein the baseline biometric history comprises a time-averaged standard deviation indicating a normal degree of variability of a particular biometric measurement of the user during prior play of the wagering game.

16. The gaming system of claim 13, wherein the selected frequency of energy comprises electromagnetic energy at a frequency of less than one Hertz applied to the player's head.

17. The gaming system of claim 13, wherein the selected frequency of energy comprises sound energy at frequencies designed to supplement the a vocal frequency of the player.

18. The gaming system of claim 13, wherein the selected frequency of energy is provided to maintain a level of 1000 to 5000 ions per cubic centimeter in the vicinity of the player's head.

19. The gaming system of claim 13, further comprising a network connection by which the baseline biometric history is loaded from a server.

20. The method of claim 1, wherein the baseline biometric history comprises a time-averaged standard deviation indicating a normal degree of variability of a particular biometric measurement of the player during prior play of the wagering game.

* * * * *